(12) United States Patent
Okuda et al.

(10) Patent No.: US 7,231,079 B2
(45) Date of Patent: Jun. 12, 2007

(54) METHOD AND SYSTEM FOR INSPECTING ELECTRONIC CIRCUIT PATTERN

(75) Inventors: Hirohito Okuda, Yokohama (JP); Yuji Takagi, Kamakura (JP); Masahiro Watanabe, Yokohama (JP); Shunji Maeda, Yokohama (JP); Minori Noguchi, Mizukaidou (JP) 3; Yoshimasa Ooshima, Yokohama (JP); Makoto Ono, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 523 days.

(21) Appl. No.: 10/050,519

(22) Filed: Jan. 18, 2002

(65) Prior Publication Data

US 2002/0113234 A1    Aug. 22, 2002

(30) Foreign Application Priority Data

Feb. 21, 2001  (JP)  ............................. 2001-045490
Sep. 26, 2001  (JP)  ............................. 2001-294482

(51) Int. Cl.
  *G06K 9/00*  (2006.01)
(52) U.S. Cl. .................................................... 382/145
(58) Field of Classification Search ................ 382/100, 382/141, 143–151; 348/86, 87, 125, 126; 356/394, 237.1–237.5, 239.7, 239.8; 256/559.39
  See application file for complete search history.

(56) References Cited

U.S. PATENT DOCUMENTS 6,466,895 B1 * 10/2002 Harvey et al. ............... 702/181
6,483,937 B1 * 11/2002 Samuels ...................... 382/144

FOREIGN PATENT DOCUMENTS

JP   62-43505    2/1987
JP   10-135228   5/1998

* cited by examiner

*Primary Examiner*—Vikkram Bali
(74) *Attorney, Agent, or Firm*—Antonelli, Terry, Stout & Kraus, LLP.

(57) ABSTRACT

For the purpose of reducing a false report and shortening inspection time, an area to be inspected is locally inspected under optimum inspection conditions. In order to avoid the number of detected defects from increasing explosively, and thereby to facilitate control of a critical defect, general-purpose layout data, which is used for producing a mask of a semiconductor wafer, is accumulated in a design information server 2. With reference to the layout data, an area to be inspected, which is inspected by a pattern inspecting apparatus 1, is divided into partial inspection areas including a cell portion and a non-cell portion. Inspection parameters are set for each of the partial inspection areas. In addition, the defect reviewing apparatus 8 obtains an inspection result of the pattern inspecting apparatus 1. When obtaining a defect image, the defect reviewing apparatus 8 identifies a position, where the defect occurred, from among a cell portion, a non-cell portion, a pattern dense portion, and the like according to layout data. Moreover, the defect reviewing apparatus 8 sets inspection parameters, such as pickup magnification of this defect, in response to a result of the identification to set a control criterion of criticality.

27 Claims, 22 Drawing Sheets

☐ DENSITY OF WIRING IS LOW
☐ DENSITY OF WIRING IS MEDIUM
▨ DENSITY OF WIRING IS HIGH

SCALE-UP

☐ DENSITY OF WIRING IS LOW
☐ DENSITY OF WIRING IS MEDIUM
▓ DENSITY OF WIRING IS HIGH

METHOD AND SYSTEM FOR INSPECTING ELECTRONIC CIRCUIT PATTERN

BACKGROUND OF THE INVENTION

The present invention relates to a pattern inspecting apparatus for inspecting a defect of an electronic circuit pattern formed on a semiconductor wafer, and in particular, to a defect-inspection control system of an electronic circuit pattern, a defect inspecting system and an defect inspecting apparatus of an electronic circuit pattern, by which man-hours set by inspection parameters (inspection conditions) in a pattern inspecting apparatus are reduced according to design information including layout data, and by which defect information detected by the pattern inspecting apparatus is managed.

While a lifetime of a semiconductor product is being shortened, and while a shift toward a multi-product production system is being performed mainly in a field of system LSI, a demand for early establishment of mass-production process conditions are more and more being increased. A defect inspecting apparatus is extremely important as a tool that inspects appearance in each process of semiconductor production, and that acquires information about a state, in which a defect occurs, to get an instruction to adjust process conditions, or to detect malfunction of a process state. As semiconductor appearance inspecting apparatuses that have already been put into practice, there are an optical foreign-material inspecting apparatus, and an optical or an electron-beam pattern inspecting apparatus, and an optical or an electron-beam defect reviewing apparatus.

As a conventional example in which a defect of an electronic circuit pattern formed on a semiconductor wafer is inspected, for example, an optical wafer defect inspecting apparatus that is described in Japanese Patent Application Laid-Open No. Sho 62-43505, and an electron beam defect reviewing apparatus that was described in Japanese Patent Application Laid-Open No. Hei 10-135288, are known. When inspecting a defect of an electronic circuit pattern using these defect inspecting apparatuses, a user is required to set and adjust various inspection parameters including set conditions of an optical system. After describing an outline of inspection for these inspecting apparatuses, setting of the inspection parameters will be described below.

In the first place, as a first example of the prior art, optical defect-inspecting technology will be described with reference to FIG. 27.

In the figure, to begin with, a semiconductor wafer 121 as an object to be inspected is secured on a stage 120. Then, while moving the stage 120, a surface of the semiconductor wafer 121 is light-scanned. Reflected light from the surface of this semiconductor wafer 121 is detected by a detector 123 through a detection optical system 122. The detected output is then stored in a memory 124 as digital data.

On the semiconductor wafer 121, a chip pattern is repeatedly copied at fixed intervals. After an image of an object point 127 to be inspected on the semiconductor wafer 121 (hereinafter the image is referred to as defect image because it is an image as an object for which a defect is inspected) is detected, and stored in the memory 124 as digital data, an image of a point 128 having the same pattern in an adjacent chip is detected as a reference image, and is stored in a memory 25. A comparator 126 compares the defect image 127 and the reference image 128, which have been stored in the memories 124 and 125, respectively, and then extracts and outputs a defect.

The example described above relates to a case where an image of the same point in an adjacent chip is detected for use as a reference image. However, in a case where a repeated pattern portion such as a memory (hereinafter referred to as cell portion) is inspected, an image, which is shifted by a repeated period, may be used. Usually, in a cell portion, as compared with comparison at the same point on a physically apart adjacent chip, comparison with an area, of which a repeated unit is shifted by one period, enables an inspection with high sensitivity. This is because as regards a difference image between the reference image and the defect image, brightness distribution of a normal portion tends to decrease, as they get nearer physically, which results in a large difference in signal intensity between the defect portion and the normal portion in an image. This can be explained by the fact that a shape gap of a pattern becomes smaller as they get nearer physically, or that a difference in coherent light intensity caused by a surface film becomes smaller as they get nearer physically, or the like.

Usually, a method, in which an image shifted by one repeated period in a repeated pattern portion is used as a reference image, is called a cell comparison method; and a method, in which an image detected at the same point in an adjacent chip is used as a reference image, is called a die comparison method.

FIG. 28 is an explanatory diagram illustrating comparison operation in the comparator 126 shown in FIG. 27. Reference numeral 130 denotes a defect image, and 131 denotes a reference image.

To be more specific, comparison logical operation is performed for binarized images 132 and 133, which have been obtained by classification into black and white according to whether or not a brightness value of an image is higher than a fixed value (=binarization threshold value), to get a comparison result 134. In this comparison result 134, not only a defect but also a component 134a caused by dispersion in pattern shape between the defect image 130 and the reference image 131, and a component 134b caused by noise are produced. Usually, detection of a component except such a defect area causes a false report. Therefore, noise removal processing is performed. Noise removal can be achieved by the following: for example, if a diameter is smaller than or equal to a fixed value (hereinafter referred to as a noise removal threshold value) in binarization images, considering it to be noise, and removing the noise. As a result of noise removal processing, as is the case with the processing result 135, only the defect is extracted.

As described above, as regards the die comparison method, noise is produced more easily than the cell comparison method. Therefore, the noise removal threshold value is required to be larger than that of the cell comparison method. This means that the defect that is smaller than a noise removal threshold value cannot be detected.

In the above description, the binarization threshold value and the noise removal threshold value, which have been described above, are called inspection parameters (inspection conditions). Setting of the inspection parameters will be described below.

FIG. 29 is a diagram illustrating an example of a screen for setting typical inspection parameters.

In the same figure, an inspection-parameter setting screen displays a wafer map 140, which explicitly shows a chip as an object to be inspected, and a cell-area setting screen 141, which magnifies the chip as the object to be inspected for displaying the chip. A user can inspect a cell area in the chip by using an inspection parameter which is different from a non-cell area, by surrounding the cell area (cell portion) 142 with a broken line in the cell-area setting screen 141 to select the cell area. To be more specific, after the cell area 142 is selected, various inspection parameters such as a detection optical system parameter or an image processing parameter in the cell area 142 are directly inputted by the manual operation on GUI, and in succession, inspection parameters of a non-cell area except the cell area is directly inputted by the manual operation on GUI in a similar manner. In the cell area 142, setting a noise removal threshold value to be smaller than the non-cell portion enables an inspection with sensitivity higher than that of the non-cell portion.

Next, procedures for setting a cell area by the manual operation will be described.

The cell area 142 is set by the following operation: placing a cursor at a desired position in a circumferential portion of an area, which is intended for the cell area 142, on the cell-area setting screen 141; clicking a mouse to define the position as a vertex of the cell area 142; and repeating the defining operation for each vertex to define a vertex group of the cell area 142. In this method, there is also a case where cell areas are dispersively located at ten positions or more in a chip area. Therefore, the manual setting is required for each cell area one by one.

Next, an electron beam type defect reviewing apparatus will be described as a second example of the prior art.

In contrast to the pattern inspecting apparatus described as the first example of the technology, which is intended for a wafer where a state in which a defect occurs is unknown, a defect reviewing apparatus detects an image of a defect position again for a wafer, of which a defect position has already been identified by a pattern inspecting apparatus, for the purpose of observing the defect in more detail.

That is to say, in the first place, the wafer is inspected by the pattern inspecting apparatus as described above, and thereby the defect position is detected. Output information of the pattern inspecting apparatus includes simple information about a defect such as a defect position on a wafer and an outline of a size.

Usually, as regards defect detection by the pattern inspecting apparatus, for the purpose of shortening inspection time, an image is not detected with magnification high enough to observe its detail as compared with a size of a defect.

The defect reviewing apparatus picks up an image of a defect position on a wafer, and a reference image corresponding to this image, with magnification high enough to observe a defect in detail using output information of a pattern inspecting apparatus as an input. Image-pickup magnification is one of the inspection parameters, which are predetermined by a user. An image is picked up with specific magnification, which has been predetermined for all defects.

Next, manual parameter-setting procedures in the defect inspecting apparatus will be described.

Such parameters are roughly classified into a parameter (hereinafter referred to as image detection parameter) which sets image pickup conditions, and a parameter (hereinafter referred to as image processing parameter) which sets image processing conditions.

A typical flowchart illustrating manual inspection-parameter setting procedures on the defect reviewing apparatus will be described. To begin with, an area to be inspected is set. The area to be inspected is defined by inputting data such as a chip layout and a chip size on a semiconductor wafer surface. Moreover, as regards some defect inspecting apparatuses, a chip is divided into a plurality of partial inspection areas (such as a cell area, and a non-cell area) for setting.

An area to be inspected is manually set using the following procedures. The above-mentioned partial inspection area, which is divided, is considered to be a rectangular for example. While displaying an image, which has been picked up on a sample surface, on an operation screen, an operator moves a stage, on which a semiconductor wafer is mounted, so that a vertex of a rectangle enters a visual field, in order to specify a rectangular partial inspection area by the manual operation. Then, the user manually specifies a vertex position of the rectangle by using a cursor, or the like on GUI as shown in FIG. 29. Performing similar manual operation for each vertex of the rectangle enables setting of the partial inspection area on the rectangle. If there are a plurality of partial inspection areas, it is necessary to perform the manual setting operation of a rectangular area repeatedly.

Next, the operator manually sets image detection parameters temporarily, detects an image at a position appropriately selected from the area to be inspected, and then judges whether or not image quality is good by a visual inspection on GUI. In this case, if the image quality is not good, the image detection parameters are manually set again.

Next, as regards the image detection parameter, which has been set, the operator manually sets image processing parameters temporarily on GUI, and executes a temporary inspection. After executing the inspection, the operator checks a position of a detected defect, and inspects a state in which the image processing parameters are set. If there are more false reports than expected, this means that sensitivity is too high. Therefore, the sensitivity is reduced. On the other hand, if the number of detected defects is too few, or if a standard defect could not be detected, the sensitivity is increased.

Each manual operation of resetting of the image processing parameters, re-execution of a temporary inspection, and a recheck of an inspection result is executed repeatedly until the parameter adjustment is completed, and until desired conditions for judgment are satisfied as follows: the number of false reports becomes a fixed number or less; or the number of false reports becomes a fixed number or less within a range that a standard defect is found; or the like.

As described as the prior art, including selection which method should be executed (the cell comparison method or the die comparison method), concerning general inspection parameters, even if the operator tries to divide an area to be inspected into many partial inspection areas, and tries to set a different inspection parameter for each partial inspection area, setting of each partial inspection area is forced to depend on manpower, which hinders efficient setting. Division by manual operation into many partial inspection areas of which an inspection parameter is different substantially, and an inspection by manual setting the inspection parameter which is different for each partial inspection area, become impossible substantially. This is disadvantageous in the following points.

Firstly, explosive increase in the number of detected defects cannot be avoided. Depending on pattern density, a size of a fatal defect is different. To be more specific, if pattern density is high, it is important that even a defect having a smaller size can be detected reliably. Nevertheless, if defect detection sensitivity is manually set high enough to be appropriate to an area where a pattern is dense, and if this is applied to an entire surface of an area to be inspected, the number of detected defects will become 1000 or more, resulting in difficult control.

Secondly, inspection parameters cannot be optimized for each position. As an example of inspection parameters, critical parameters as described above are mentioned.

Other than the example, as regards parameters related to image detection conditions, if a defect reviewing apparatus, which has been introduced as the second example of the prior art, is described as an example, a defect size, which is the most important for control, is determined depending on roughness and fineness of a pattern as described above. Image-pickup magnification, which is used when detecting an image, should be set so that a defect having this image size is suited for a pickup image size. However, under present circumstances, because an image is detected at fixed image-pickup magnification, a case where magnification becomes too low or too high as compared with a defect size often arises.

In addition, as regards the conventional procedures, there is a problem that manual setting of an area to be inspected requires great efforts. Conventionally, when a chip area is divided by manual operation into a plurality of partial areas, such as a cell area and a non-cell area, if a number of divisions is large, manual setting of an area to be inspected becomes difficult substantially. Moreover, there is also a problem that manual setting and manual adjustment of parameters for each divided partial inspection area require great efforts.

As described above, it is important to divide an area to be inspected into a plurality of partial inspection areas so that an inspection parameter, which is different for each partial inspection area, is set for an inspection. Or, it is important to set an inspection parameter for a specific pattern in an area to be inspected to inspect the specific pattern. However, conventionally, there was the problem that great efforts are required for realizing it, or that it cannot be realized practically.

SUMMARY OF THE INVENTION

The present invention provides a defect-inspection control system for inspecting an electronic circuit pattern, a defect inspecting system and an apparatus for inspecting an electronic circuit pattern, which solve the problems to improve efficiency of setting of partial inspection areas in an area to be inspected, and to enable optimization of inspection parameters that are set for each partial inspection area easily.

To be more specific, the present invention has a configuration comprising: an inspection area setting unit which divides an area to be inspected into at least two partial inspection areas, each of which has different inspection conditions; an inspection condition setting unit which sets inspection conditions for each partial inspection area that is set by the inspection area setting unit; and an inspection executing unit which executes inspection under the inspection conditions, which are set by the inspection condition setting unit, for each partial inspection area set by the inspection area setting unit.

In addition, the inspection area setting unit is configured to divide an area to be inspected into a plurality of partial inspection areas according to a layout pattern.

In addition, the present invention has a configuration comprising: an inspection area setting unit which divides an area to be inspected, for example, into function blocks, or into blocks each of which has substantially the same wiring density, or into blocks each of which has different criticality, according to layout data; an inspection condition setting unit which sets inspection conditions for each partial inspection area that is set by the inspection area setting unit; and an inspection executing unit which executes inspection under the inspection conditions, which are set by the inspection condition setting unit, for each partial inspection area set by the inspection area setting unit.

This enables a large reduction in efforts, which are required to divide an area to be inspected into a plurality of partial inspection areas.

Moreover, the present invention has a configuration comprising: an inspection area setting unit which divides an area to be inspected into a plurality of partial inspection areas, each of which has different inspection conditions, according to layout data; an inspection condition setting unit which sets initial values of inspection conditions, adjustment rules of the inspection conditions, and convergence conditions of the inspection conditions, for each partial inspection area set by the inspection area setting unit; an image detection unit for detecting an image at a point to be inspected; an inspection executing unit which divides an image, which has been detected by the image detection unit, into images, each of which corresponds to each partial inspection area, by the inspection area setting unit in each partial inspection area, and that processes them using initial values of the inspection conditions to detect a defect for each partial inspection area; and an image storing unit for storing an image at a point where there is a defect.

This enables a large reduction in efforts, which are required to set inspection parameters for each partial inspection area.

These and other objects, features and advantages of the invention will be apparent from the following more particular description of preferred embodiments of the invention, as illustrated in the accompanying drawings.

DESCRIPTION OF THE PREFERRED EMBODIMENTS

Preferred embodiments of the present invention will be described with reference to drawings hereinafter.

Figure 1:
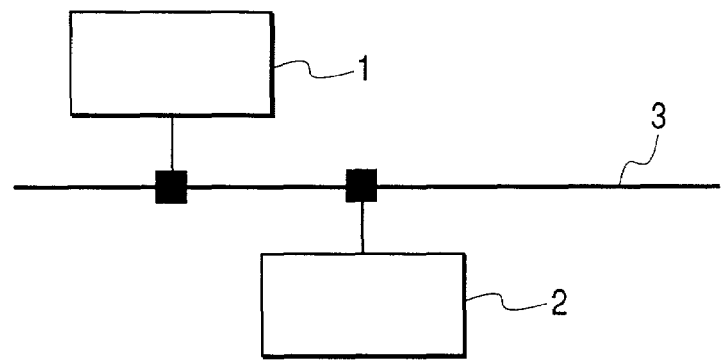
FIG. 1 is a block diagram illustrating a defect-inspection control system for inspecting an electronic circuit pattern according to a first embodiment of the present invention.

FIG. 1 is a configuration diagram illustrating a defect-inspection control system for inspecting an electronic circuit pattern according to a first embodiment of the present invention. Reference numeral 1 denotes a pattern inspecting apparatus; 2 denotes a design information server; and 3 denotes a network such as LAN.

In the figure, the pattern inspecting apparatus 1 is connected to the design information server 2 through the network 3, which permits data to be transmitted to and received from the design information server 2. The design information server 2 stores the layout data of a semiconductor wafer to be inspected. The pattern inspecting apparatus 1 divides an area to be inspected on a chip in the semiconductor wafer into each of function blocks (for example a cell portion and non-cell portions) on the basis of the layout data 29, provides a database of inspection parameters 40 and decides inspection parameters (inspection conditions are consisted from condition of optical system and condition of image processing) for each function block or each wiring width by searching inspection parameter in corresponding to each function block from the database of inspection parameters.

Figure 2:
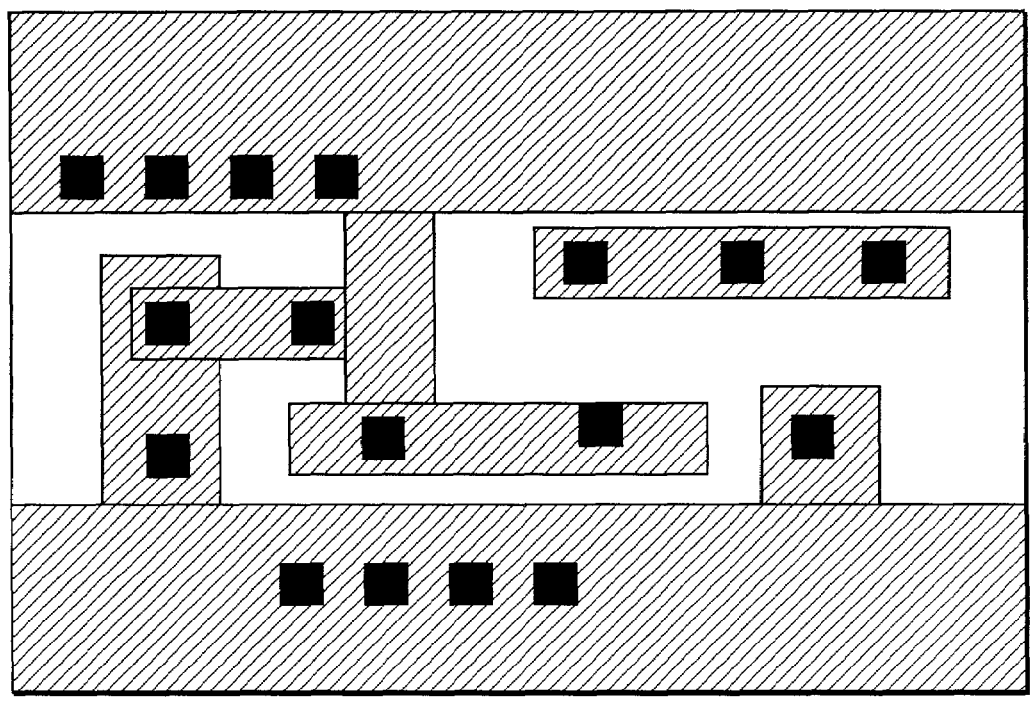
FIG. 2 is an explanatory diagram illustrating a layout pattern.

The layout data 29 is a general-purpose data used for manufacturing a mask for the semiconductor wafer and is vector data comprising numerical values such as coordinates, and widths, of wiring ends for wiring placement in each layer. A pattern, which is processed from layout data 29 so as to form an image, is called a layout pattern. One example is shown in FIG. 2. Such layout pattern can be combined from layout data easily.

A technique for dividing an area to be inspected into a plurality of partial inspection areas, each of which has different pattern density (for example different wiring width), on the basis of layout data will be described below.

Figure 3:
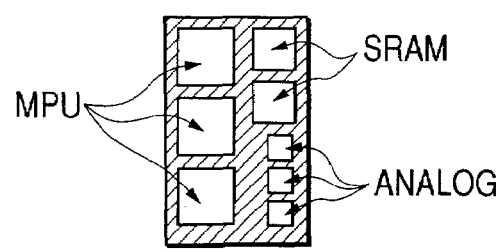
FIG. 3 is a diagram illustrating an example of module placement in a chip.

As a simplest technique, a method for dividing an area to be inspected into each of function blocks (for example a cell portion and non-cell portions),as partial inspection areas according to layout data can be considered. The layout data has a hierarchical structure, which is modularized for each function block. As shown in FIG. 3, a system LSI has a plurality of design modules in a chip. In addition, a cell portion may also be placed dispersively. It is possible to extract each module area, including a cell portion, from the layout data. To be more specific, in general, data S of area to be inspected can be divided into the following partial inspection area data according to the layout data described for each module.

Figure 23:
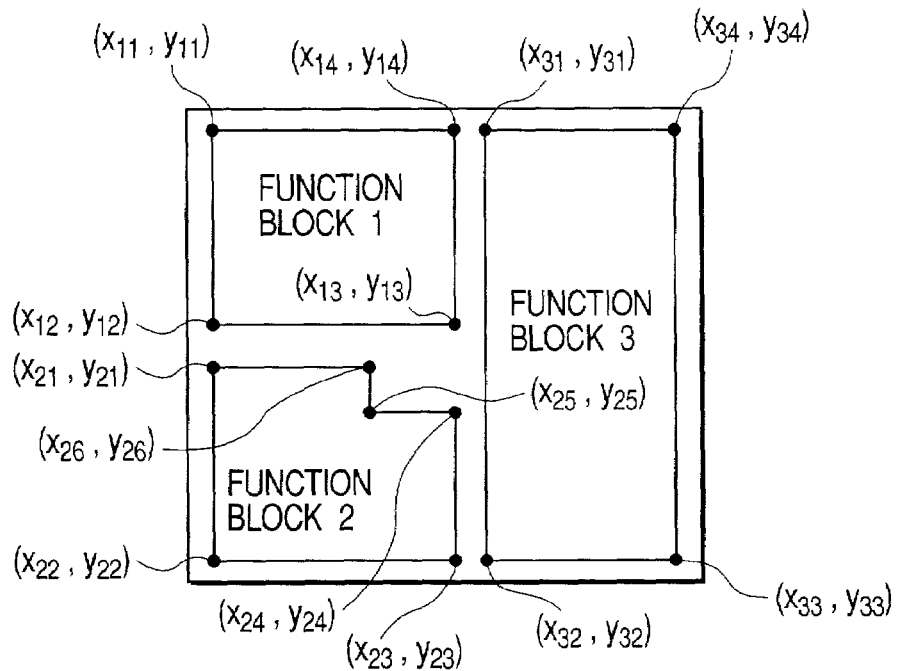
FIG. 23 is a diagram illustrating arrangement of function blocks 1 through 3 in a chip and vertex coordinates of each function block 1~3.

As above described, the procedures for dividing a chip layout into function blocks on the basis of layout data will be described with references to FIGS. 23 and 24. FIG. 23 is a diagram illustrating arrangement of function blocks 1 through 3 in a chip and vertex coordinates of each function block 1~3. In FIG. 23, vertex coordinates of function block n (n=1,2,3) are expressed as $(x_{n1}, y_{n1})$, $(x_{n2}, y_{n2})$, . . . .

Figure 24:
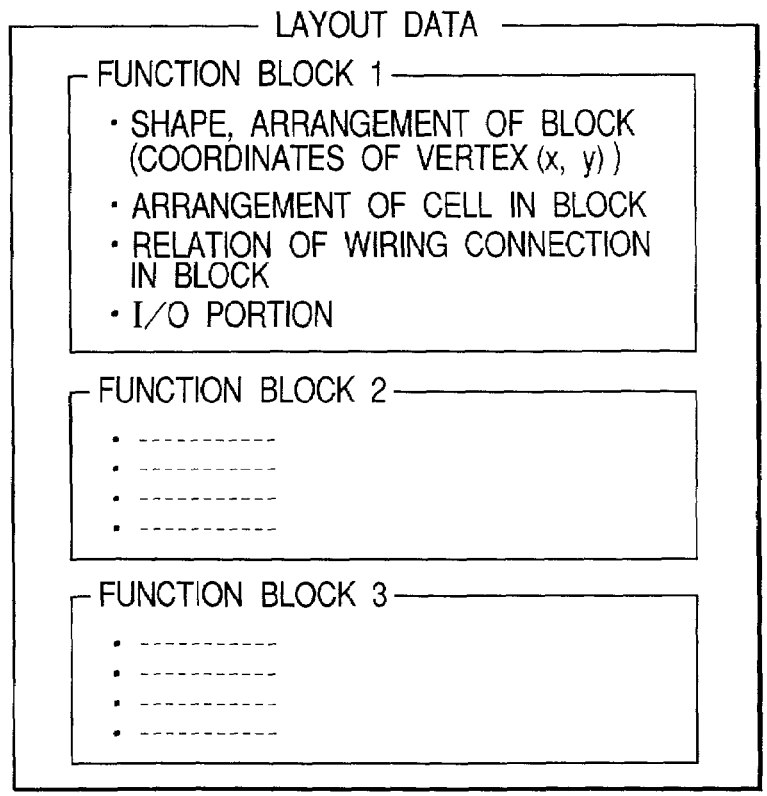
FIG. 24 is a diagram schematically illustrating layout data corresponding to the chip in FIG. 23.

FIG. 24 is a diagram schematically illustrating layout data corresponding to the chip in FIG. 23. The layout data is modularized on function block basis, and further has hierarchical structure in which a higher module is defined by nest structure of the module. In the data on a function block basis, the following are described: a shape and arrangement of a function block (in examples of FIGS. 23 and 24, vertex coordinates); relation of wiring connections of a lower function level (called cell); information about an I/O portion; and the like.

In general, the information about a shape and arrangement of a function block (in the examples of FIGS. 23 and 24, vertex coordinates) is data that is specified by a CAD tool when a layout designer of LSI designs arrangement of a function block. The information can be used for general purposes.

Figure 9:
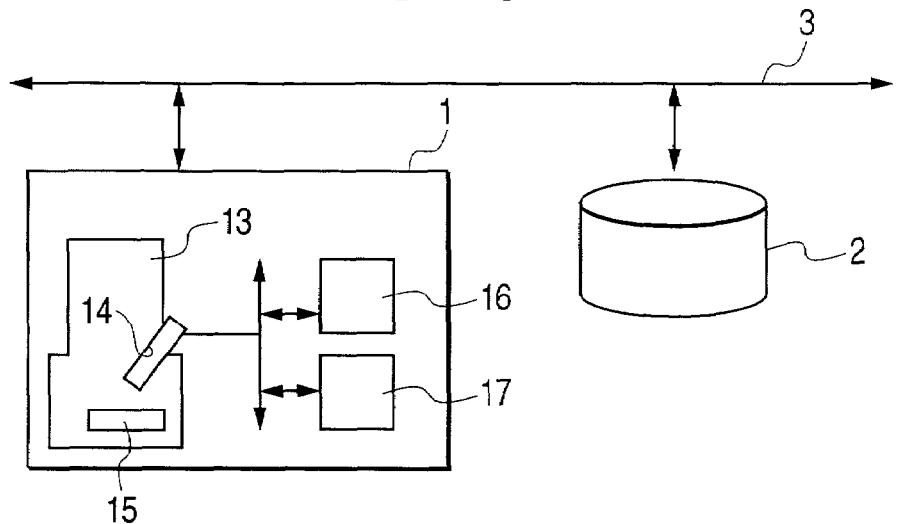
FIG. 9 is a block diagram illustrating a defect inspecting apparatus and a defect inspecting system used for inspecting an electronic circuit pattern according to a first embodiment of the present invention.

According to the present invention, a control computer (for example 17 as shown in FIG. 9) in a pattern inspecting apparatus 1 can identify an area on a function block basis by reading out information about a shape and arrangement of a function block from layout data 29 stored in a design information server 2. Further, the control computer is controlled conditions of the detection optical system and conditions of the image processing unit.

Figure 22:
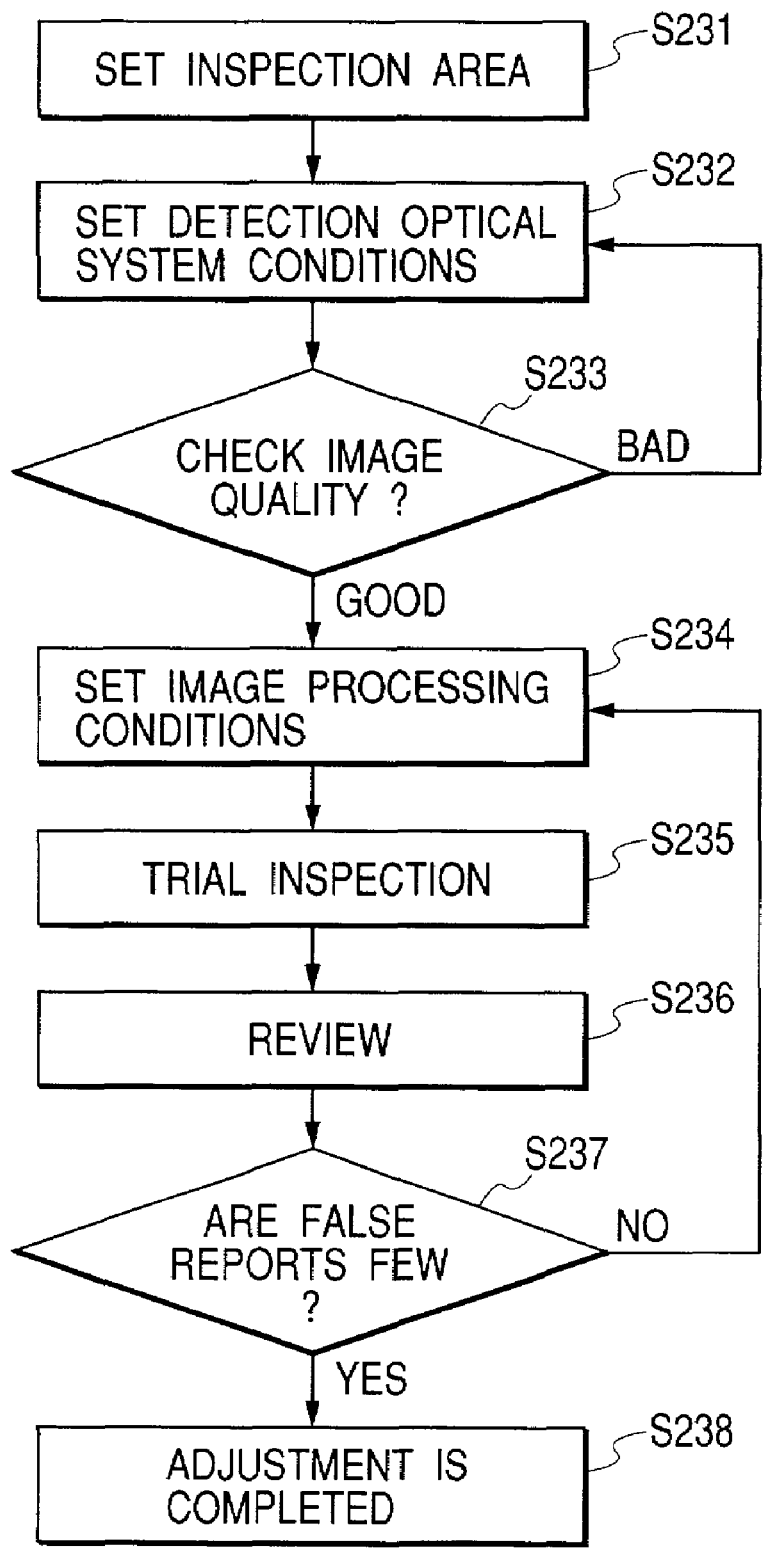
FIG. 22 is a flowchart illustrating parameter adjustment procedures in defect inspection of an electronic circuit pattern.

A flowchart of procedures for setting inspection parameters according to the present invention will be described with reference to FIG. 22. In the first place, an area to be inspected is set by identifying area of each function block on the control computer of the pattern inspecting apparatus 1 (step S231). How to set the partial inspection area will be specifically described with reference to FIG. 25. To begin with, to the pattern inspecting apparatus, the user inputs a kind of a inspection object (wafer) inserted on a stage to the computer by using an input unit (for example keyboard). Needless to say, a kind of inspection object may be automatically inputted to the computer by using a reader as the input unit. Next, the control computer searches layout data of the kind of the inspection object, which has been input by the user, in order to check whether or not the layout data exists in the layout data base 29.

Figure 4A:
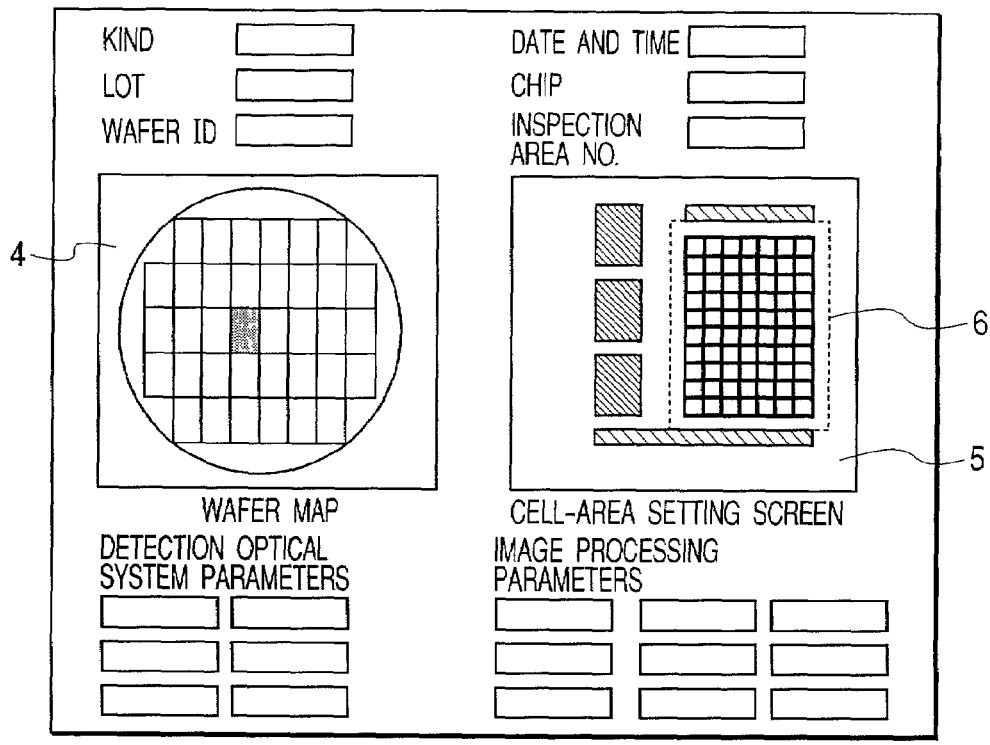
FIG. 4 is a diagram illustrating one exemplification of an inspection-parameter changing screen according to the first embodiment shown in FIG. 1.
Figure 4B:
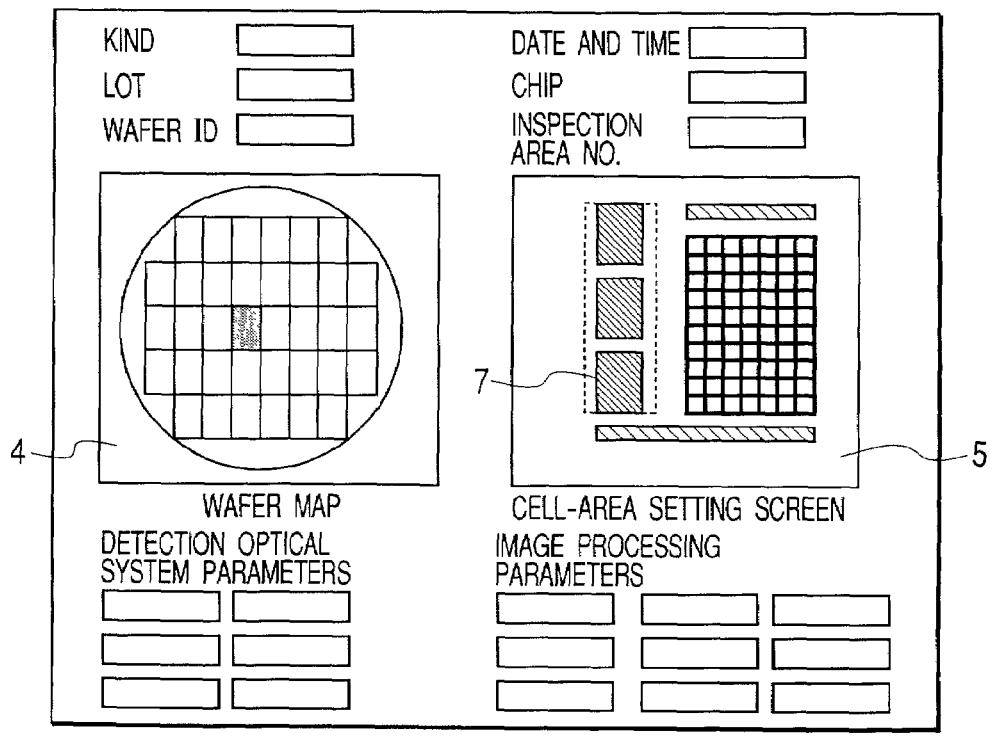

Next, if the layout data of the appropriate kind exists in the layout data base 29, the control computer reads out information about a shape and arrangement of function block on a chip from the layout data base 29 (S262), and then displays the information read out from the layout data base 29 for the user as shown in FIGS. 4(*a*) and 4(*b*) (S263). After that, the user judges whether or not the displayed function block area is required to be changed (corrected) (S264). If the area is required to be changed, the user changes the area for the computer on GUI (S265). But the control computer can decide almost all the partial inspection areas without changing the area (S266).

Figure 26:
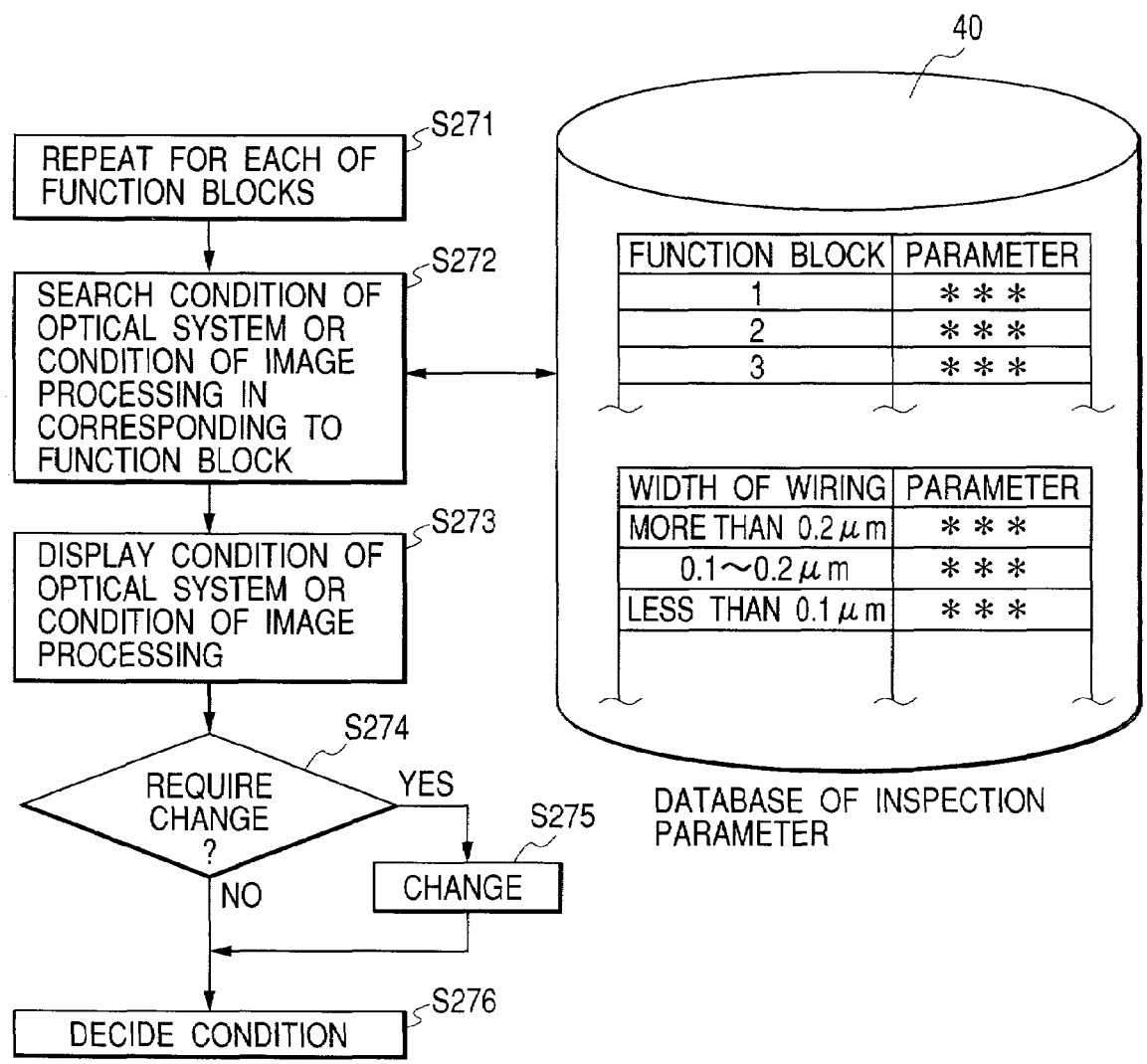
FIG. 26 is a flowchart illustrating a process flow for setting inspection parameters in corresponding to each function block.

Next, a method and an apparatus for setting of inspection conditions for each divided partial inspection area (S232, S234) will be described by using FIG. 26. In the first place, the control computer of the pattern inspection apparatus 1 sets the conditions of detection optical system and the conditions of image processing, individually for each function block of kind to be inspected. For this reason, in a step S271, the control computer repeats the settings of inspection conditions for each divided partial inspection area. Then, the control computer searches an inspection parameter, which corresponds to the function block to be inspected, in order to check whether or not the parameter is registered in an inspection parameter data base 40 (S272).

In the inspection parameter database 40, a parameter, which is appropriate to the corresponding function block, has been registered for each function block beforehand. For example, the following settings can be considered: for a function block of which a wiring rule is fine, detection sensitivity is set to be sensitive; and for a function block of which a wiring rule is comparatively large, the detection sensitivity is set to be insensitive. If LSI including the same function block has ever been inspected in the past, and if an inspection parameter at that time has been registered into the database 40, it is possible that the control computer applies the inspection parameter that has been registered. In this way, as many inspection parameters corresponding to each of many function blocks has been registered into the database 40, the control computer can set automatically the inspection parameters for almost all the function blocks.

In addition, the control computer may register the detection sensitivity on the basis of a wiring rule of a function block into the database 40. In this case, even if the LSI including the same function block has not been inspected so far, if LSI including a function block having the same wiring rule has ever been inspected, and if a inspection parameter in corresponding to the wiring rule at that time has been registered, it is possible that the control computer applies the inspection parameter that has been registered into the database 40.

Next, the computer displays the inspection parameter that has been searched in corresponding to the function block from the inspection parameter database 40 (S273). The user judge whether or not it is necessary to change (correct) the displayed inspection conditions (conditions of detection optical system, and conditions of image processing) (S274). If it is necessary to change the inspection conditions, the user changes them for the computer (S275). But, the control computer can decide the inspection conditions without changing them for almost all the function blocks by searching from the database 40 (S276). Therefore, it is possible to reduce to a minimum the number of function blocks that the user must change the inspection conditions on GUI.

In the pattern inspection apparatus, the control computer being controlled the detection optical system sets image detection parameters as condition of the detection-optical system by searching in corresponding to the function block from the inspection parameter database 40 (S232) and the detection optical system detects an image at a position appropriately selected from the each divided partial inspection area in corresponding to each function block. Then, the user judges whether or not image quality is good by a visual inspection in order to judge whether or not it is necessary to change (correct) the condition of the detection optical system (S233). In this case, if the image quality is not good, the image detection parameter as the condition of the optical system is changed. But, the number of function blocks that the user must change the image detection parameter as the condition of the detection optical system is very little. Incidentally, the image detection parameter is a parameter for detecting an appropriate image by the detection optical system. For example, in the case of the pattern inspection apparatus, the image detection parameters include illumination intensity of an UV or DUV light source, focused state of illumination light, detection magnification, regulation of polarization, regulation of filter, sensitivity of image sensor, and the like.

Figure 27:
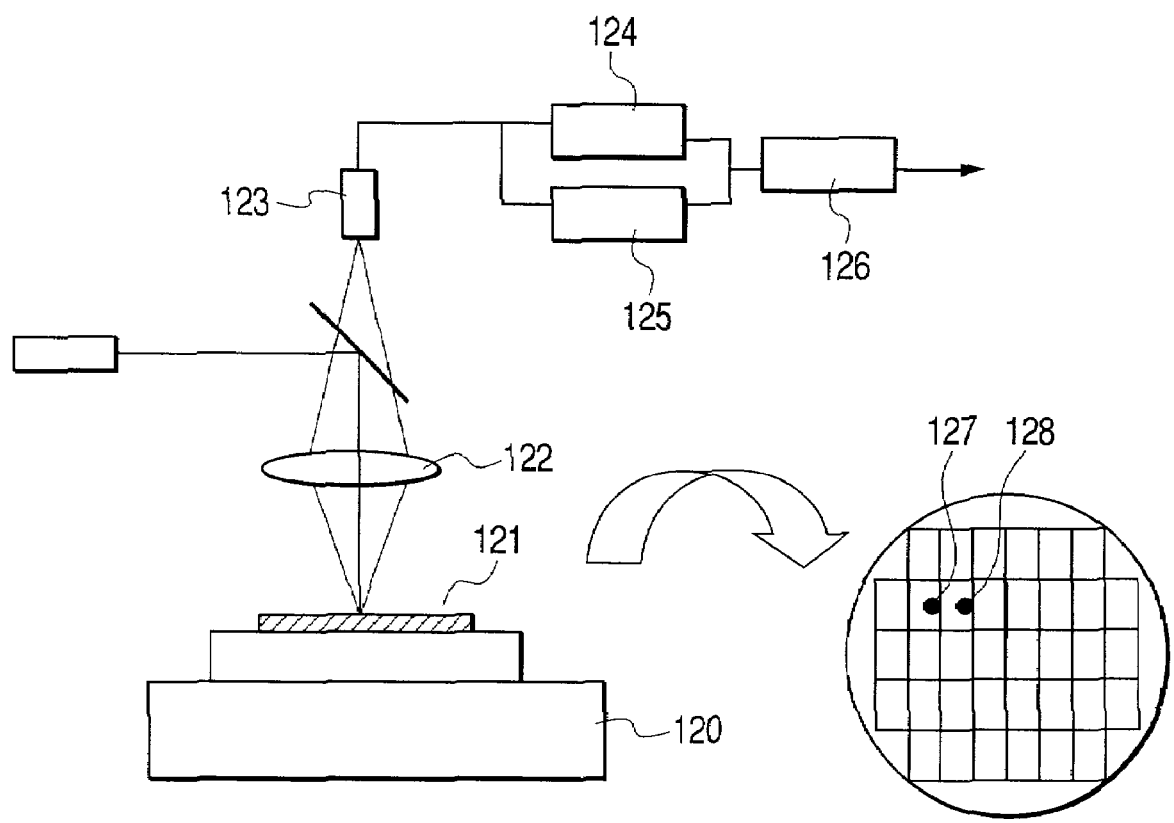
FIG. 27 is a configuration diagram illustrating one example of a conventional pattern inspecting apparatus.
Figure 28:
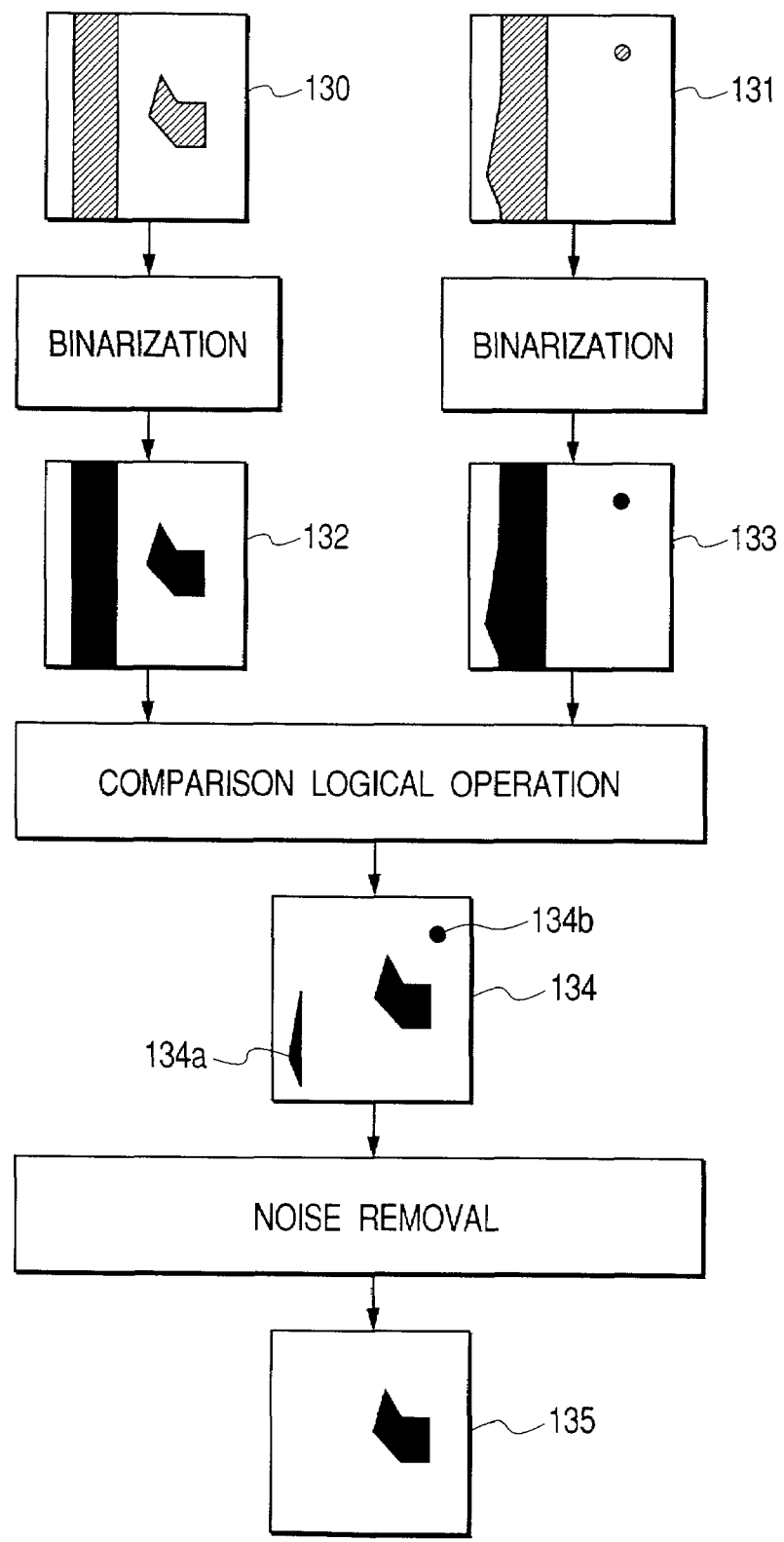
FIG. 28 is an explanatory diagram illustrating a comparison operation process of a comparator shown in FIG. 8.
Figure 29:
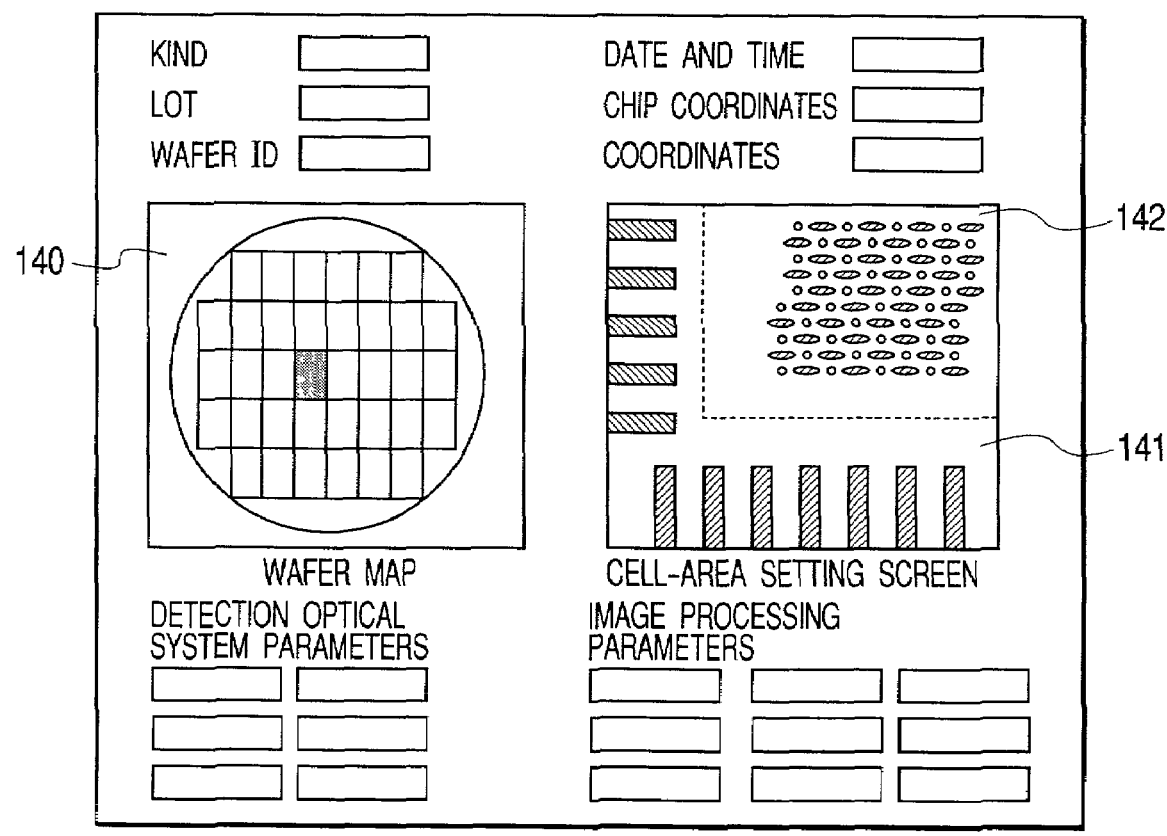
FIG. 29 is a diagram illustrating one example of a conventional inspection-parameter setting screen.

Next, in the state of setting the image detection parameter, the control computer being controlled the image processing unit sets image processing parameters as condition of the image processing by searching in corresponding to the function block from the inspection parameter database 40 (S234) and the image processing unit 124~126 as shown in FIG. 27 executes a temporary image processing for image signal detected by the detection optical system and displays the result of image processing on GUI as shown in FIGS. 6(*a*) and 6(*b*) (S235). After executing the image processing, the user checks a position of a detected defect, and inspects a state in which the image processing parameters are set (S236). In this step, the number of function blocks that the user must change the image processing parameter as the condition of the image processing is very little. If there are more false reports than expected (S237), this means that sensitivity is too high. Therefore, the user changes so as to reduce the sensitivity. In addition, for example, when detecting a minute defect more than necessary, the image processing parameter is changed so that a noise removal size is made larger. Or, for example, when detecting a false report that is long and narrow only in one of x, y directions, it is considered that a noise removal size of one of the x, y directions is made larger. After specifying defects, which should be detected on the wafer, beforehand as standard defects, the parameters may also be changed so that detection sensitivity is lowered within a range that the standard defects can be detected. On the other hand, if the number of detected defects is too few, or if a standard defect could not be detected, the sensitivity is increased. Incidentally, the image processing parameters is a parameter for detecting a truth defect from an image detected by the image sensor of the detection optical system. The image processing parameters include, for example, a judge threshold value, which is used for extracting only a defect portion from a differential image signal between a detected image signal and a reference image signal; a noise removal threshold used for removing an minute area, which does not relate to a defect, as noise; and a parameter for decreasing sensitivity at an edge.

FIG. 4 is a diagram illustrating one exemplification of an inspection-parameter changing screen which the partial inspection area and the inspection conditions have been automatically set by using the layout data 29 and the database of inspection parameter 40. In FIG. 4, on the partial inspection area changing screen, a wafer map 4, which explicitly indicates a chip to be inspected, and the cell-area setting screen 5, which magnifies and displays the chip to be inspected, and the like, are displayed. FIG. 4(*a*) shows an inspection-parameter changing screen for one partial inspection area 6 in the cell-area setting screen 5; FIG. 4(*b*) shows an inspection-parameter changing screen for the other partial inspection area 7 in the cell-area setting screen 5 concerning the same area to be inspected. On either of the screens in FIGS. 4(*a*) and 4(*b*), a frame, which indicates each of the partial inspection areas 6 and 7 set according to the layout data, is displayed in a detected image while they are overlaid.

In this manner, in the pattern inspecting apparatus 1 (FIG. 14), the partial inspection area 6 is inspected on the basis of the inspection parameters, which have been decided on the screen shown in FIG. 4(*a*); and the partial inspection area 7 is inspected on the basis of the inspection parameters, which have been decided on the screen shown in FIG. 4(*b*).

Figure 5:
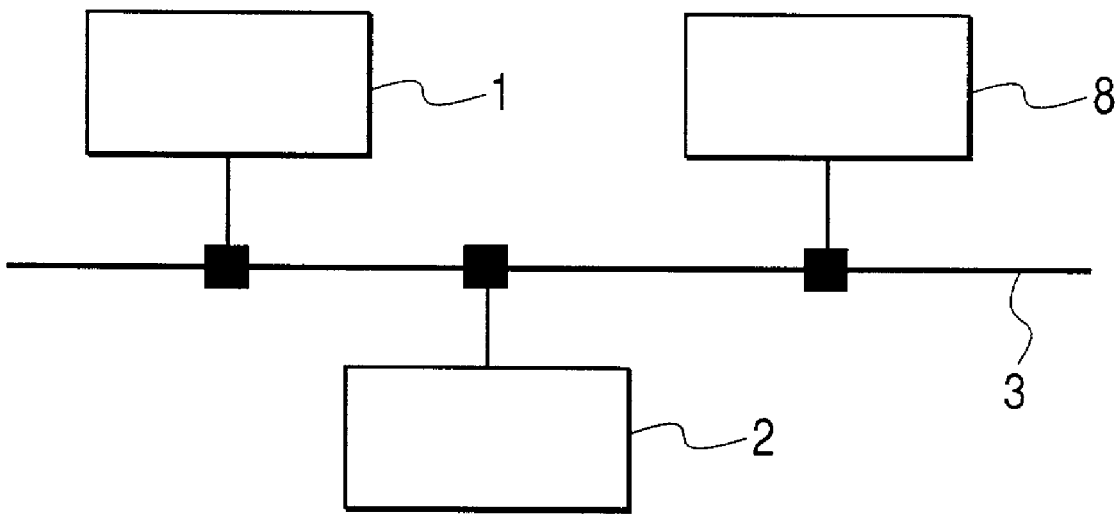
FIG. 5 is a block diagram illustrating a defect-inspection control system for inspecting an electronic circuit pattern according to a second and a third embodiment of the present invention.

FIG. 5 is a configuration diagram illustrating a defect-inspection control system for inspecting an electronic circuit pattern, according to a second embodiment of the present invention. Reference numeral 8 denotes a defect reviewing apparatus. Similar reference numerals have been used for similar parts corresponding to FIG. 1. Therefore, repeated description will be omitted.

In the figure, in the second embodiment, in addition to the configuration shown in FIG. 1, the defect reviewing apparatus 8 is connected to a LAN 3, which permits data to be transmitted and received between the pattern inspecting apparatus 1 and the design information server 2. Additionally, the design information server 2 stores design information for each kind of products to be inspected and for each process of the products to be inspected.

Targeting a wafer, on which a position of a defect is already known, the defect reviewing apparatus 8 detects an image again at the defect position for the purpose of observing the defect in more detail. More specifically, the position of the defect, which has been detected by the pattern inspecting apparatus 1, is transferred to the defect reviewing apparatus 8 as inspection-result information. The inspection-result information is text information, and comprises a defect ID (Identification) and X, Y coordinates of the defect.

The defect reviewing apparatus 8 acquires an image at each defect position recorded in the inspection-result information. After that, when acquiring an image of each defect, the defect reviewing apparatus 8 determines inspection parameters such as image-pickup magnification in response to characteristics (cell/non-cell, pattern density, etc.) of an area where there is the defect. For this reason, before image detection, layout data is obtained from the design information server 2. A user inputs information such as a kind and a process of the product to be inspected on an operation screen of the defect reviewing apparatus 8. The defect reviewing apparatus 8 retrieves layout data of the targeted kind and process, which have been inputted, from the design information server 2 and acquires it. Then, according to the acquired layout data, the defect reviewing apparatus 8 generates partial inspection area data. Here, it is assumed that the partial inspection area data is completely the same as that described in the first embodiment.

Next, a method for changing two kinds of inspection parameters for each partial inspection area on the basis of such partial inspection area data will be described.

Two kinds of the inspection parameters, which will be changed, are an image detection mode and an image-pickup magnification. Meaning of the inspection parameters and a purpose of the change for each position will be described.

The image detection mode is a parameter for specifying whether or not a reference image is detected.

The cell portion includes the same repeated patterns. Therefore, if an image of the cell portion is picked up and stored beforehand, it is not necessary to detect the reference image for each defect ID every time, and it is possible to use the stored image as the reference image repeatedly. When trying to detect a reference image newly, it is necessary to perform the following steps: moving a stage, on which a semiconductor wafer is placed, to a desired position; and irradiating an image-pickup area with an electron beam to detect an image. Therefore, as compared with a case where the reference image stored in a storage device is diverted repeatedly, longer time will be required. Thus, as regards a mode in which a reference image is diverted, it is advantageous because an inspection time can be shortened to a large extent.

Hereinafter, a mode, in which a reference image is stored and diverted, is called "reference-image reserve mode"; and a mode, in which a reference image is detected for each defect ID every time, is called "reference-image detection mode". Setting the "reference-image reserve mode" and the "reference-image detection mode" for a cell area and a non-cell area respectively in an area to be inspected permits an inspection time to be shortened to a large extent.

The image-pickup magnification is magnification at which an image is detected. Since review work is intended for detailed observation of a defect, appropriate image-pickup magnification should be set taking a size of the defect into consideration. However, if there is no information about the defect size, it is not possible to set appropriate magnification for a defect having an arbitrary size. Therefore, practically, image-pickup magnification is set so that the image-pickup magnification becomes appropriate to a defect size for which observation is most important. The size, for which observation is most important, can be determined according to a reference size for judging criticality, which is determined by an average wiring interval.

Next, a defect-inspection control system for inspecting an electronic circuit pattern according to a third embodiment of the present invention will be described.

The third embodiment also has a configuration as shown in FIG. 5. However, in addition to it, the third embodiment enables flexible adjustment of a partial inspection area as compared with the first and the second embodiment described above. In the first and the second embodiment, in order to perform completely automatic setting of a partial inspection area according to layout data, flexible adjustment of the partial inspection area is not always possible. In the third embodiment, a defect position, which has been detected by the pattern inspecting apparatus, is reviewed by the defect reviewing apparatus. After that, review results are given to inspection parameter setting of the pattern inspecting apparatus as feedback.

More specifically, the position of the defect, which has been detected by the pattern inspecting apparatus 1 in FIG. 5, is transferred to the defect reviewing apparatus 8 as inspection-result information. The defect reviewing apparatus 8 performs a review, and then generates review-result information, in which information about each defect such as a kind of a defect is added to each defect. The pattern inspecting apparatus 1 can read the review-result information from the defect reviewing apparatus 8 as needed.

Figure 6A:
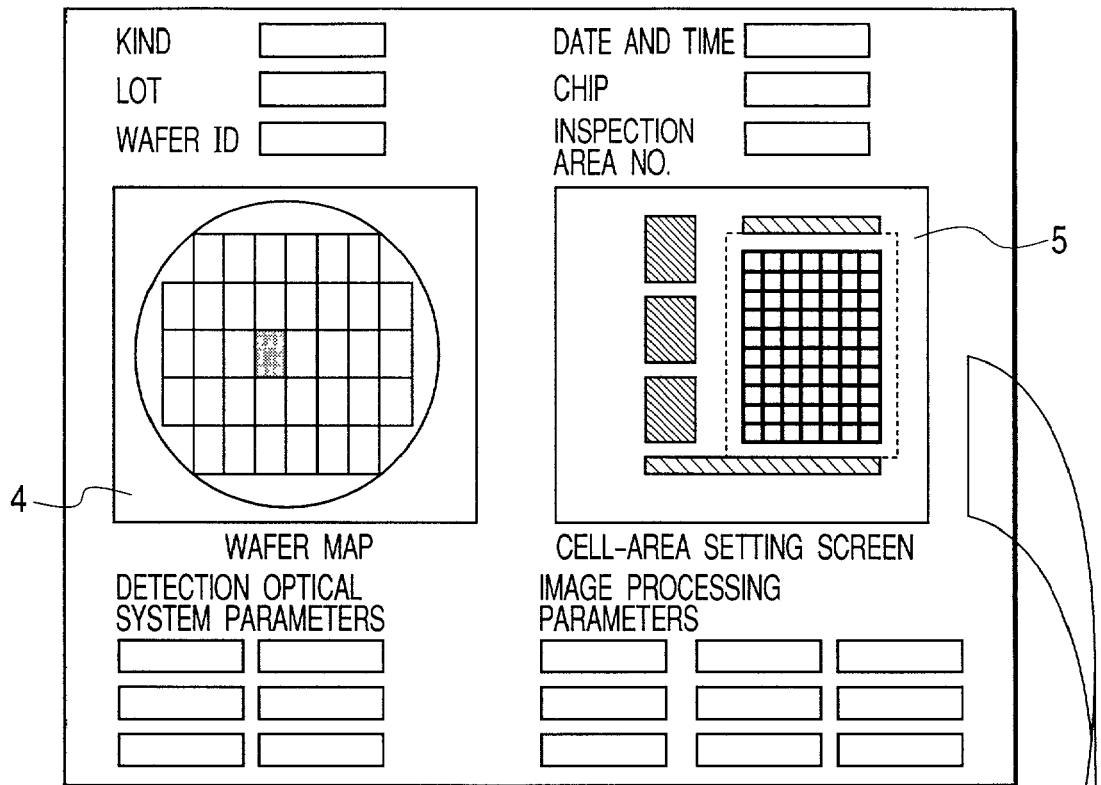
FIG. 6 is a diagram illustrating one exemplification of an inspection-parameter changing screen in a defect-inspection control system for inspecting an electronic circuit pattern according to the third embodiment of the present invention.
Figure 6B:
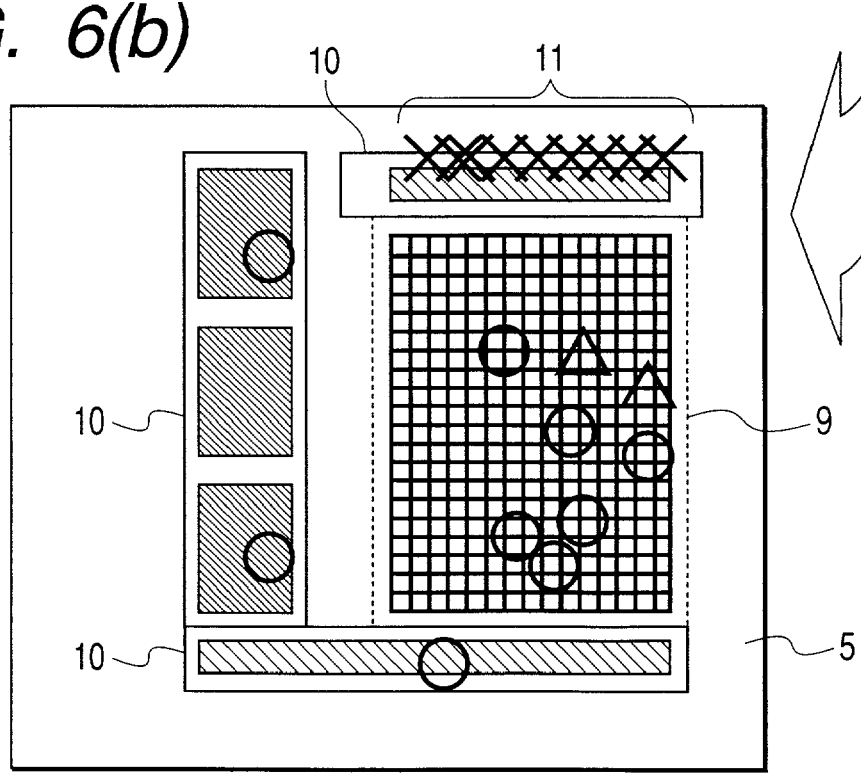

FIG. 6(a) is a diagram illustrating an inspection-parameter changing screen of the pattern detection device 1, which has acquired the review-result information in the third embodiment. Similar reference numerals have been used for similar parts corresponding to FIG. 4. In addition, FIG. 6(b) is a diagram illustrating a scaled-up screen of the cell-area setting screen 5 shown in FIG. 6(a). Reference numeral 9 denotes a cell portion; 10 denotes a non-cell portion; and 11 denotes a defect group.

On the screen shown in FIG. 6(a), a wafer map 4, in which a chip to be inspected is indicated explicitly, a cell-area setting screen 5, which displays this chip after scaling up, and the like, are displayed. On the cell-area setting screen 5, as shown in FIG. 6(b), at least one of a setting state, layout data, detected image, and review-result information, relating to a partial inspection area, are displayed in parallel, or they are overlaid. In this case, the overlay display is to make a plurality of maps semitransparent and to superimpose them for displaying. The overlay display enables us to observe a manner, in which the maps overlap, easily.

In FIG. 6(b), in a cell portion 9 surrounded by a thick broken line, a setting state of the partial inspection area, a detected image, and review-result information are overlaid. A frame of a thick broken line, which specifies the cell portion 9 as a partial inspection area, and a frame of a thick solid line, which specifies a non-cell portion 10 as a partial inspection area, are based on layout data accumulated in a design information server 2 (FIG. 5). The frames are overlaid on images of the cell portion 9 and the non-cell portion 10 on the cell-area setting screen 5. Different inspection parameters are set for the cell portion 9 and the non-cell portion 10. For the cell portion 9, the inspection parameter is set so that detection sensitivity becomes high. On the other hand, for the non-cell portion 10, the inspection parameter is set so that the detection sensitivity becomes low. Symbols including ○, Δ, and X indicate review-result information, which is overlaid with the cell portion 9 and the non-cell portion 10. In this case, such review-result information corresponds to kinds of defects as an example; ○, Δ, and X indicate a foreign material, a dent, and a false report, respectively. Positions of the symbols indicate occurrence positions of these defects.

A user can check whether or not the number of detected defects are too many, or whether or not the number of the detected defects are too few unnaturally, and the like (that is to say, whether or not detection sensitivity is appropriate), by observing the cell-area setting screen 5.

In this case, it is assumed that the use can edit the partial inspection area freely. More specifically, the following are possible: addition of a new partial inspection area; deletion of an existing partial inspection area; and addition and deletion of a partial area to an existing partial inspection area.

Moreover, a false report may occur at a specific point in an area to be inspected with concentration. As its cause, the following is considered: accuracy of a pattern shape becomes unstable at a specific point, caused by a process; or dispersion of a film thickness becomes large at a specific point, which causes large dispersion of coherent light intensity. In FIG. 6(b), a defect group 11 indicated by one non-cell portion 10 corresponds to this. When the user observes the cell-area setting screen 5, and if an exceptional pattern is found in distribution of defects, the user can check whether or not it is a false report, by scaling up occurrence points of the defects. The exceptional pattern includes the following: defects occur on a specific point with a concentration unnaturally; defects line up on a straight line; and the like. When displaying an image by scaling up to check the image, and if it is judged that detection is not required, it is possible to reduce the number of defects, which do not require detection, by setting a partial inspection area newly again in circumference of an area where false reports have occurred with a concentration, and by decreasing inspection sensitivity in the partial inspection area.

Figure 7:
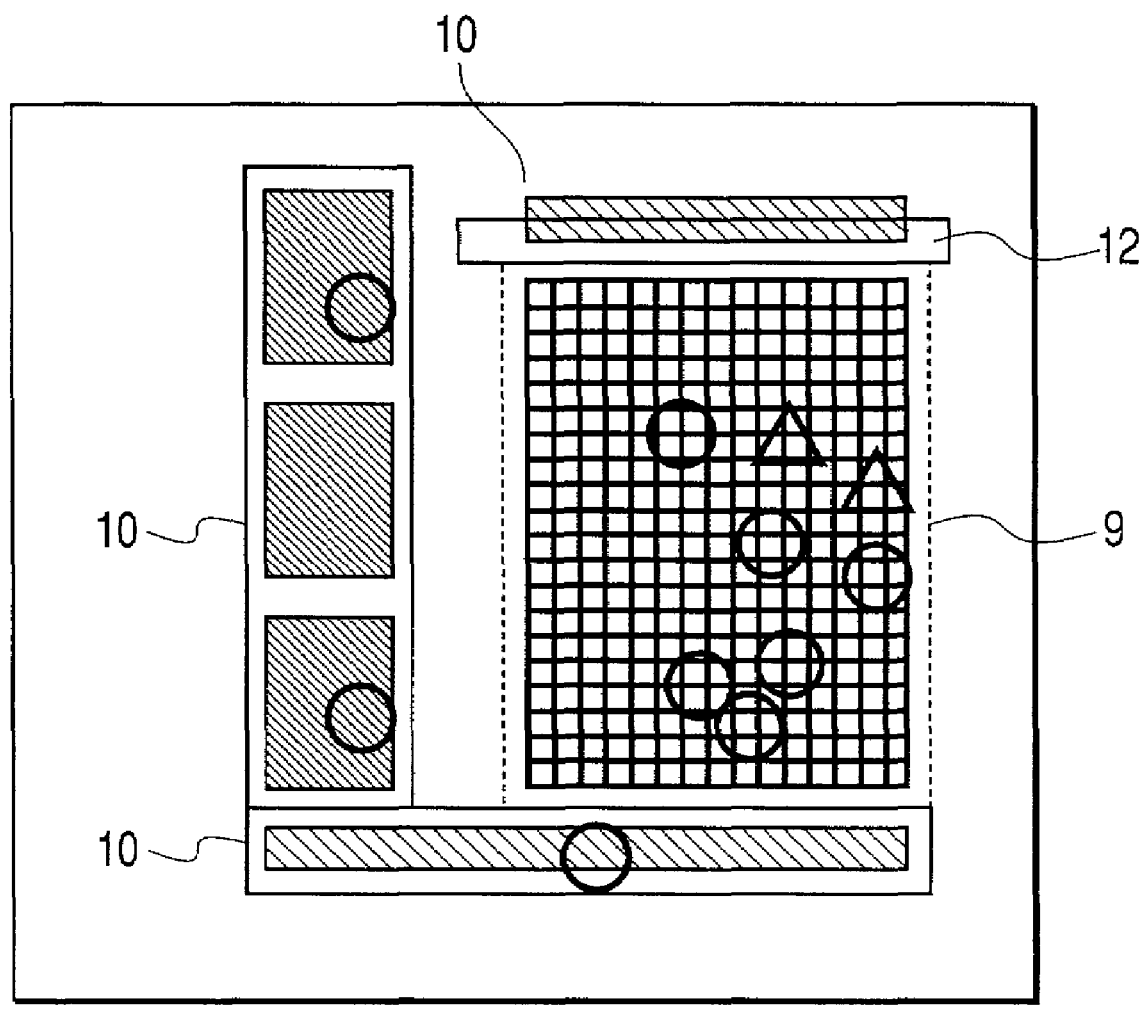
FIG. 7 is a diagram illustrating a cell-area setting screen of the inspection-parameter changing screen, which has been reedited from a partial inspection area of the inspection-parameter setting screen shown in FIG. 6.

FIG. 7 is a diagram illustrating results of reedition of an partial inspection area (partial inspection area of the non-cell portion 10, where false reports have occurred unnaturally, shown by X), which has been set on the cell-area setting screen 5 shown in FIG. 6(b) in the manner described above. On the cell-area setting screen 5 after reedition excluding false reports shown by X, the inspection results and the review-result information described above are overlaid. As a result of excluding false reports shown by X from the inspection area, the partial inspection area 12 is scaled down as compared with the partial inspection area shown in FIG. 6. As a result, an output of the false report group 11 shown in FIG. 6 is restrained.

Next, an embodiment of a defect inspecting apparatus and an inspection system, which are used for inspecting an electronic circuit pattern, according to the present invention will be described. In this case, the defect inspecting apparatus and the inspection system divide an inspection area into a plurality of areas, each of which has a different degree of coarseness and minuteness of a pattern, automatically according to layout data in order to facilitate optimization of an inspection parameter for each divided area.

As described above, layout data, which is used in an embodiment describe below, is also general-purpose data used for mask production of a semiconductor wafer. The layout data-is vector data that describes placement of wiring in each layer by numerical values such as coordinates and widths of wiring end points. Data that is processed from layout data so as to form an image is called a layout pattern. The technology, which combines a layout pattern from layout data, is broadly used for verification of layout design, and for other purposes.

Figure 8A:
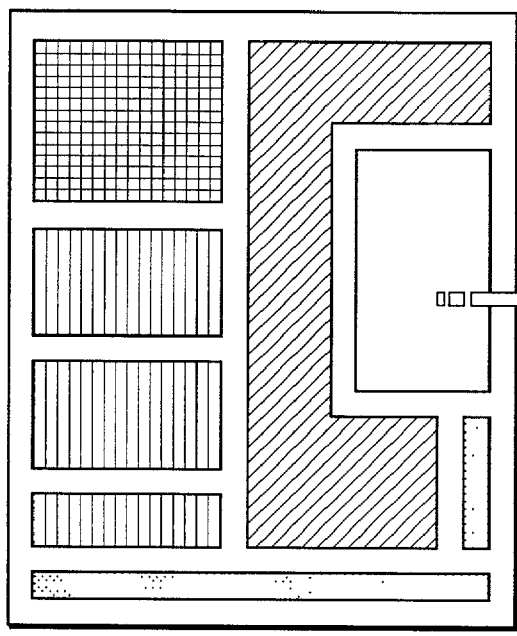
FIG. 8 is a diagram for explaining a layout pattern.
Figure 8B:
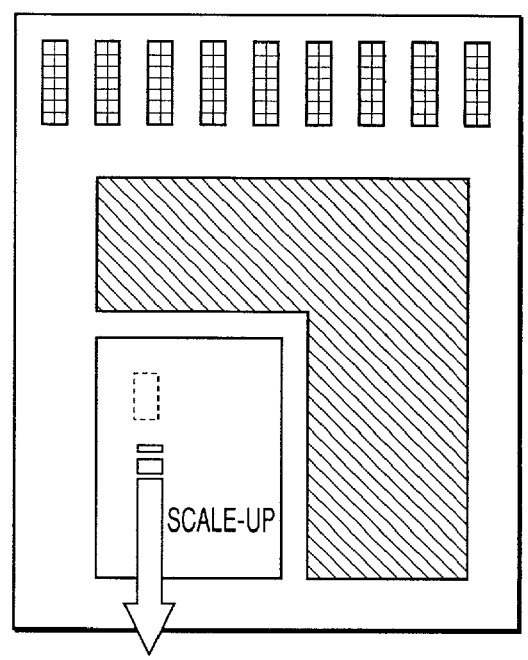
Figure 8C:
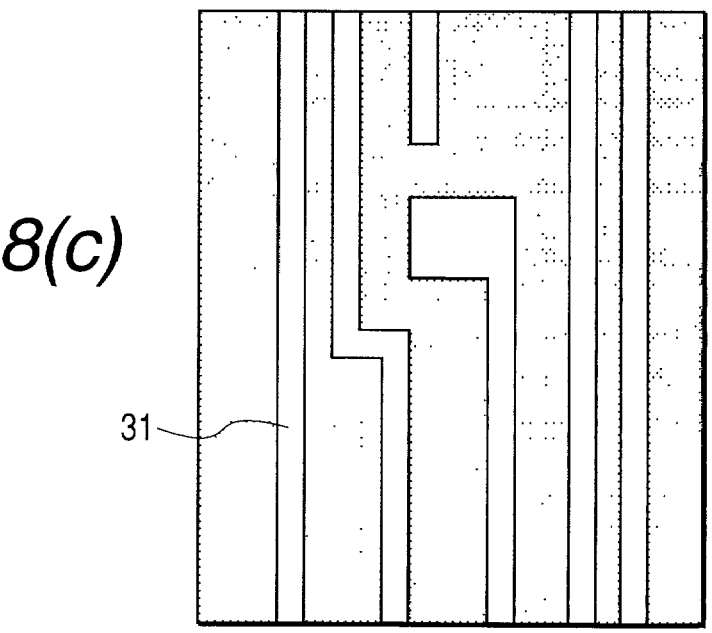

FIG. 8 is a diagram illustrating one exemplification of such a layout pattern; FIG. 8(b) is a diagram in which one part of a pattern shown in FIG. 8(a) is scaled up; and FIG. 8(c) is a diagram in which one part of a pattern shown in FIG. 8(b) is scaled up.

FIG. 9 is a configuration diagram illustrating a defect inspecting apparatus and a system, which are used for inspecting an electronic circuit pattern, according to a first embodiment of the present invention. Reference numeral 13 denotes a scanning electron microscope; 14 an image detector; 15 a semiconductor wafer; 16 a storage device; and 17 an image-processing computer. Similar reference numerals have been used for similar parts corresponding to FIG. 1.

In the figure, the pattern inspecting apparatus 1 comprises the scanning electron microscope 13 (hereinafter it is simply called electron microscope), and detects an image of the semiconductor wafer 15 as an object to be inspected, which is mounted in a cabinet of the electron microscope 13, using the image detector 14. The detected image is transferred to the image-processing computer 17 through a bus. The image-processing computer 17 processes the detected image to detect a defect of an image and to classify the defect. In addition, the detected image and the like can also be stored in the storage device 16. The design information server 2, in which layout data is accumulated, is configured to be capable of transferring data between the design information server 2 and the pattern inspecting apparatus 1 mutually through a storage medium such as a LAN and a DAT.

Figure 10:
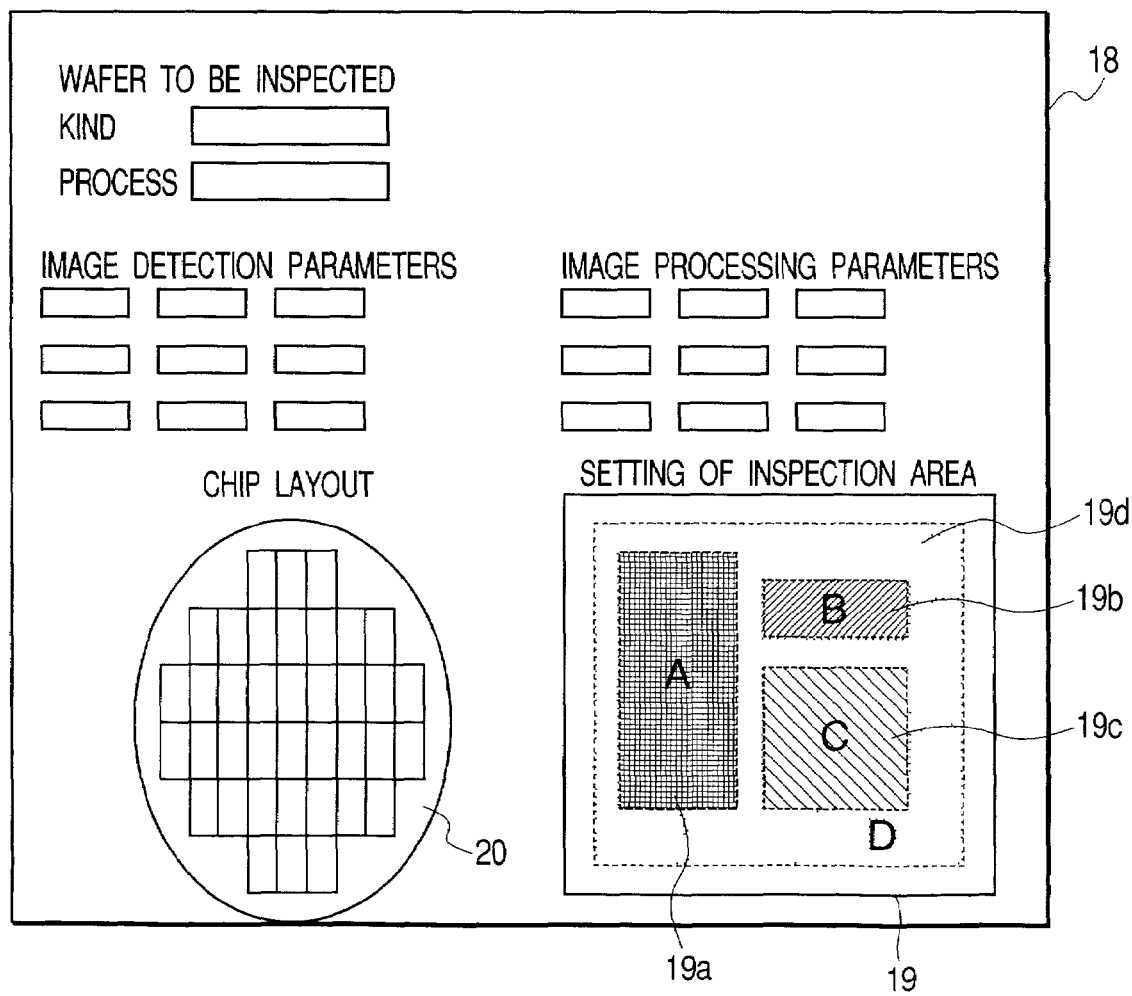
FIG. 10 is a diagram illustrating one exemplification of an inspection-parameter screen in the embodiment shown in FIG. 9.

The image-processing computer 17 comprises a user interface for instruction to control the pattern defect inspecting system. FIG. 10 is a diagram illustrating one exemplification of an inspection-parameter changing screen 18, which is one part of the user interface of the image processing computer 17.

A image-processing computer 17 sets a kind, a process, an image detection parameter, an image processing parameter, and an inspection area, relating to a semiconductor wafer as an object to be inspected, and displays the result of the inspection parameters set in this inspection-parameter changing screen 18. When the user inputs a kind of a semiconductor wafer as an object to be inspected, the image processing computer 17 transfers layout data of the target kind from the design information server 12 to the storage device 16. In addition, if another wafer of the same kind has already been inspected, and if its layout pattern is stored in the storage device 16, it is not necessary to transfer the layout pattern to the storage device 16 again. In this case of an electron-beam visual inspecting apparatus 13, the image detection parameter includes detection magnification, correction conditions of astigmatism, a probe electric current value, an acceleration voltage, a gain, offset correction quantity, and the number of times an image is added. The image processing parameters is substantially same in above case.

The details will be described later. However, the image processing computer 17 automatically divides an area to be inspected into a plurality of areas, each of which has different pattern density, according to the layout data, and then prompts the user to confirm and change the divided areas. In addition to it, the image processing computer 17 prompts to set an inspection parameter for each of the divided areas.

On the inspection-parameter changing screen 18 shown in FIG. 10, results of automatic division of the area to be inspected 19 is shown. In this case, this area to be inspected 19 is divided into a partial area 19a of A, a partial area 19b of B, a partial area 19c of C, and a partial area 19d of D. In the area to be inspected 19, a layout pattern of the whole chip is displayed. In addition to it, calculation results of the area division, which has been calculated by the image-processing computer 17 according to the layout data, is also displayed. The partial areas 19a through 19d, which are shown in dotted lines, are the calculation results of the area division. Each of the partial areas 19a through 19d has a similar degree of pattern density in each area. Attributes of each of the divided partial areas 19a through 19d (for example, an average line interval, and the like) are displayed on the screen. The user can also change the area division, which has been calculated by the image-processing computer 17, on a screen of the area to be inspected 19 as needed.

Next, a method for automatically dividing the area to be inspected 19 into a plurality of areas, each of which has different pattern density, according to the layout data will be described.

FIG. 11 is a diagram illustrating a first exemplification of such an automatic dividing method.

Figure 11A:
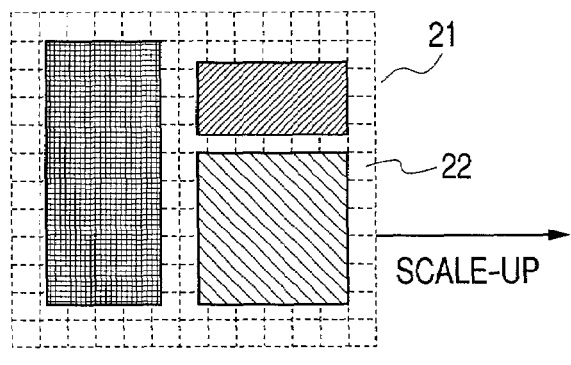
FIG. 11 is a diagram illustrating one exemplification of a method for dividing an area to be inspected in the embodiment shown in FIG. 9.
Figure 11B:
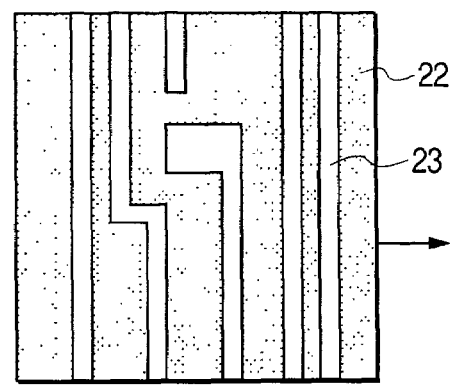

This exemplification is a method for dividing a chip layout into lattices, and for grouping areas having a similar degree of wiring area density in each lattice. In the first place, as shown in FIG. 11(a), a chip area (area to be inspected 19) 21 is divided into lattices. FIG. 11(b) is a diagram illustrating a scaled-up layout pattern of a wiring 23 in one lattice 22. Concerning this layout pattern, for the purpose of referring to the diagram easily, it is assumed that only several wires 23 are included in the lattice 22. However, in reality, from the viewpoint of calculation time, it is desirable to set this lattice 22 in a rectangular area having a larger area.

Next, a ratio of an area of wiring is calculated for each lattice.

To be more specific, the following is calculated: wiring density=an area of wiring/an area of a lattice.

Figure 11C:
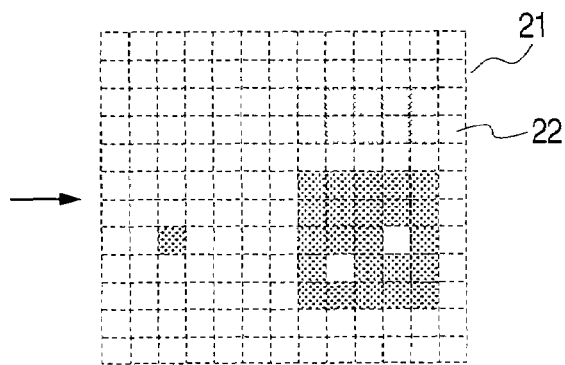

The wiring density can be determined from an area of wires 23 included in the lattice 22. Or, the wiring density can be calculated directly from a distribution range of a pattern, which is described in the layout data, without forming a layout pattern from the layout data. FIG. 11(c) shows a state in which the lattice 22 is colored in response to a degree of the wiring density calculated for each lattice 22 (it is shaded here as a matter of convenience). The brighter the lattice 22 is colored, the lower wiring density is shown; and the darker the lattice 22 is colored, the higher wiring density is shown.

Next, according to a degree of wiring density of each lattice 22, a label is given to the lattice 22. For example, threshold values (ThH, ThL) for judging a degree of wiring density is provided beforehand, and the threshold values are compared with wiring density D of the lattice 22.

If is D>ThH, the label is "high wiring density".
If ThH>D>ThL, the label is "medium wiring density".
If is ThL>D, the label is "low wiring density".

At the time of inspection condition setting, an inspection parameter is set for each label. For this reason, when an inspecting each lattice 22, an inspection is executed by an inspection parameter corresponding to a label given to each lattice 22. For example, for the lattice 22, to which the label "high wiring density" has been given, an inspection is executed by an inspection parameter set for the label "high wiring density".

Moreover, as another method for dividing the area to be inspected 19 (FIG. 10) into areas, each of which has a similar degree of wiring density, there is a method using Monte Carlo simulation. This will be described with reference to FIG. 12.

Figure 12A:
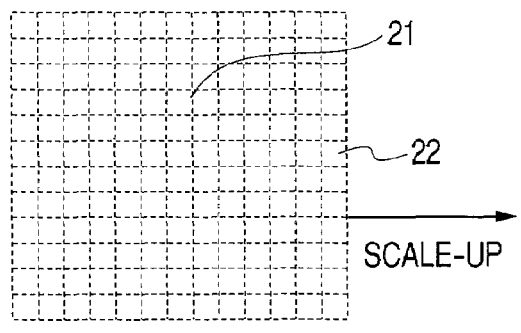
FIG. 12 is a diagram illustrating another exemplification of a method for dividing an area to be inspected in the embodiment shown in FIG. 9.
Figure 12B:
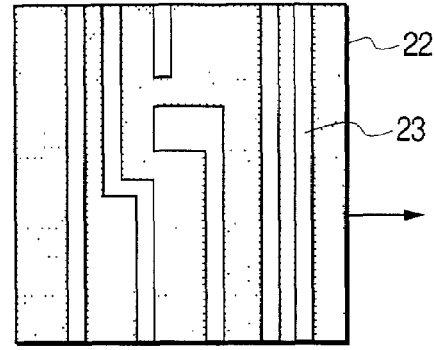
Figure 12C:
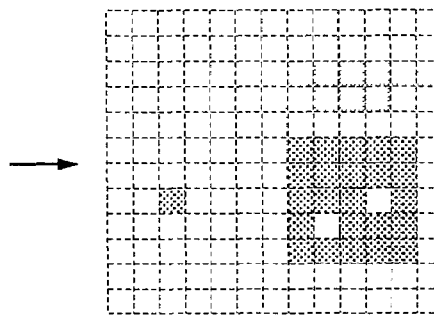

As is the case with the above description, in the first place, as shown in FIG. 12(a), an area to be inspected 21 is divided into lattices. FIG. 12(b) shows a scaled-up layout pattern of the wires 23 in one lattice 22. The following processing is performed in each lattice 22.

Figure 12D:
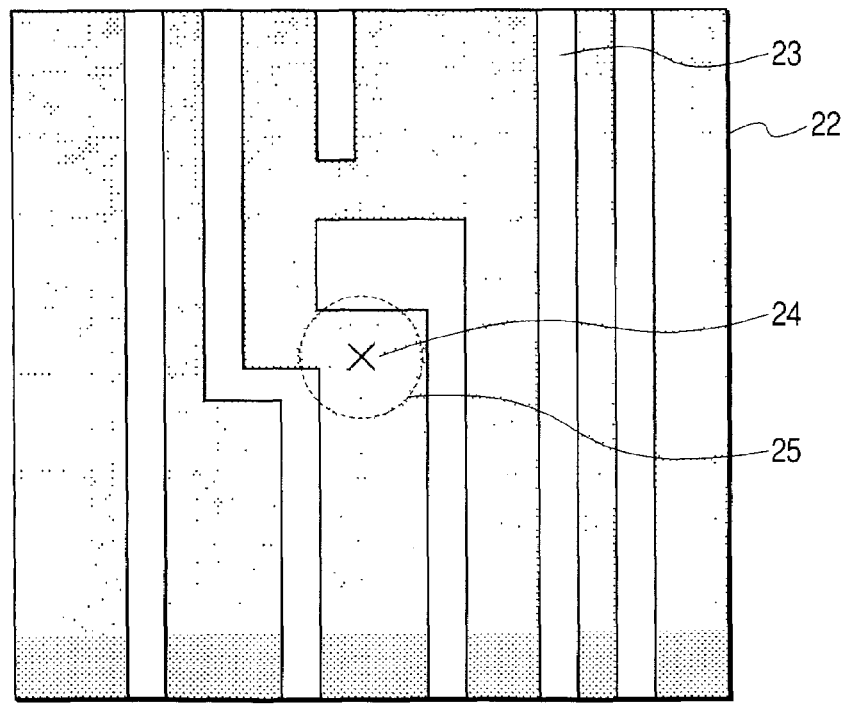

More specifically, in FIG. 12(d), which is scaled up from FIG. 12(b), a wiring-density calculation point 24 is generated at a random position in the lattice 22. In the next place, a circle 25 having a virtual radius r is set using this wiring-density calculation point 24 as its center. Then, a minimum value $r_{min}$ of radius r is determined so that a pattern of the wires 23 is included inside this virtual circle 25. This minimum value rd min means a distance from the wiring-density calculation point 24 to an edge of a nearest wire 23. The higher the minimum value $r_{min}$ increases, the sparser a pattern of the wire 23 in proximity to the wiring-density calculation point 24 becomes. On the contrary, the lower the minimum value $r_{min}$ decreases, the denser the pattern of the wire 23 in proximity to the wiring-density calculation point 24 becomes.

In this manner, the wiring-density calculation point 24 for wiring density calculation is generated in the lattice 22 at a random position multiple times, and then a mean value of minimum radii $r_{min}$ of the virtual circle 25, which is drawn using the wiring-density calculation point 24 as its center, is determined. If the number of occurrence times is larger, the value will approximate to average density of patterns of wires 23 in the lattice 22.

Thus, density of the pattern of the wires 23 in each lattice 22 can be calculated. FIG. 12(*c*) shows results of the calculation. The method using the Monte Carlo simulation is superior to the method for calculating an area of a pattern of the wires 23 in the lattice 22, which has been described above, from the viewpoint of calculation time. Actually, as regards the method for calculating an area, it is necessary to calculate an area of all wiring patterns of the area to be inspected 21. However, in the case of the method using Monte Carlo simulation, only calculation processing at the wiring-density calculation point 24, which has been generated at random, is required. This is the reason of the superiority.

Figure 13:
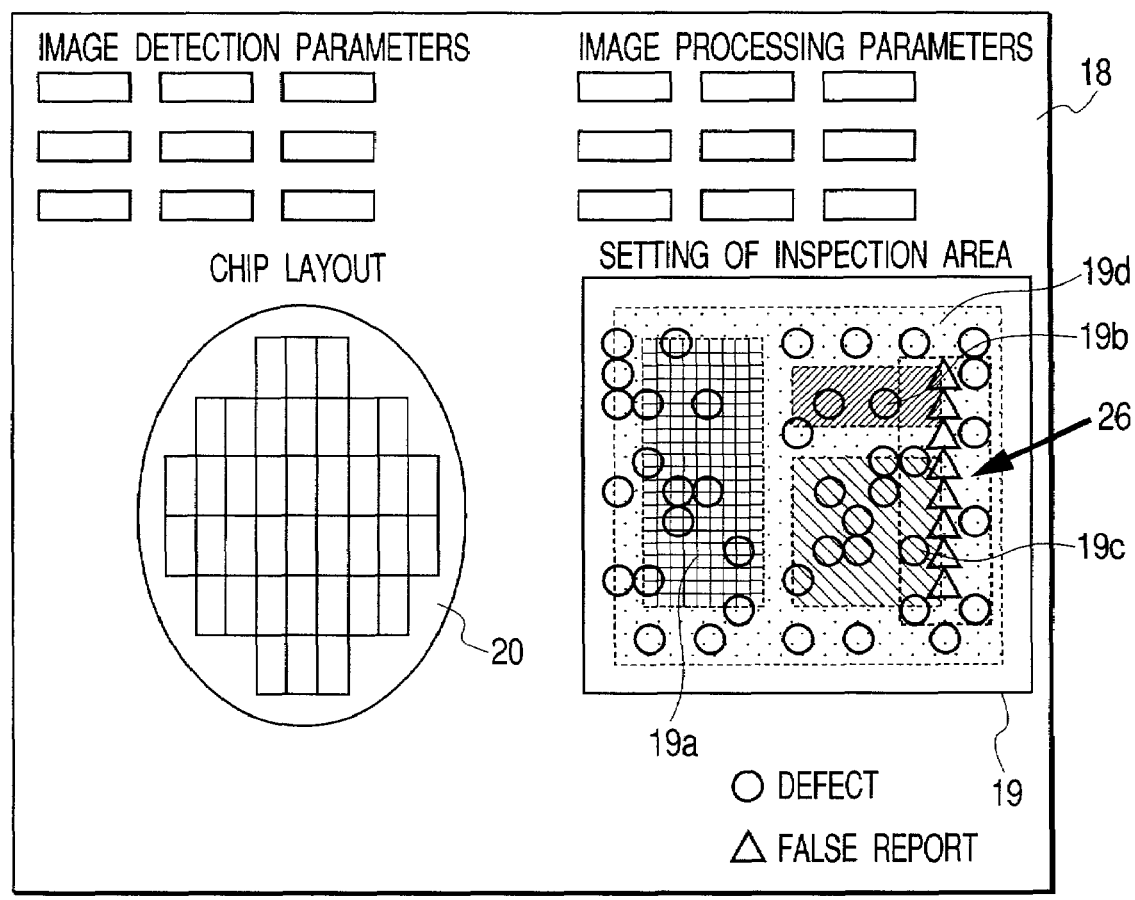
FIG. 13 is a diagram illustrating a state in which layout data and a result of review in the embodiment shown in FIG. 9 are overlaid on an inspection-parameter setting screen.

As described above, results of the division of the area 21 to be inspected, which has been calculated according to the layout data, is indicated on the inspection-parameter setting screen 18 shown in FIG. 10. In addition, after executing trial inspection (step 204 in FIG. 25), as shown in FIG. 13, review results of a defect (that is to say, a position and a kind of a defect) is overlaid on the inspection-parameter setting screen 18. In this case, a true defect is indicated by a symbol "○"; and a false report of a defect is indicated by a symbol "Δ".

The user can check results of area division, review results of a defect, and layout data, which have been displayed from the inspection-parameter setting screen 18. Additionally, because true defects and false reports are displayed using different symbols, it is possible to grasp easily that, for example, false reports occur with a concentration in a specific area on a chip indicated by an arrow 26. Moreover, since they are superimposed (overlaid) with a layout pattern, it is possible to grasp relation between an occurrence position of a false report and a layout easily. As a result of observation of the display screen, if the user found out that false reports have occurred with a concentration at a specific point, the user can set a new partial inspection area by manual operation so as to decrease inspection sensitivity at a place in proximity to it. In addition, for a plurality of chips, a state in which review results are superimposed may be displayed. The superimposition enables the user to observe a phenomenon that cannot be observed easily from a state in which defects have occurred in an individual chip.

Figure 14:
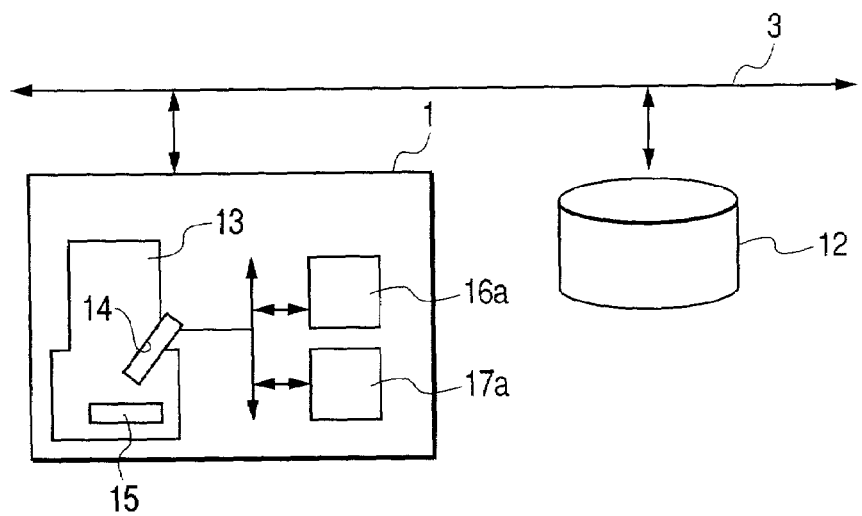
FIG. 14 is a block diagram illustrating a second embodiment of a defect inspecting apparatus and a defect inspecting system used for inspecting an electronic circuit pattern, according to the present invention.

FIG. 14 is a configuration diagram illustrating a defect inspecting apparatus and a system, which are used for inspecting an electronic circuit pattern, according to a second embodiment of the present invention. Reference numeral 16*a* denotes a storage device; and 17*a* denotes an image-processing computer. Similar reference numerals have been used for similar parts corresponding to FIG. 9.

In contrast to the first embodiment shown in FIG. 9, in the second embodiment, an area to be inspected is divided into function blocks (or design modules) according to layout data. An inspection parameter is set for each divided function blocks. The inspection parameter is then registered in an inspection parameter database. As a result, even for other kinds of semiconductor wafers, if a function block is the same, it is not necessary to set an inspection parameter newly. To be more specific, when inspecting a new kind of a semiconductor wafer, whether or not an inspection parameter of a function block included in the layout data has already been registered in the inspection parameter database is searched for. If the inspection parameter has already been registered, it is set as an inspection condition.

In FIG. 14, the image processing computer 17*a* and the storage device 16*a* have functions of the image processing computer 17 and the storage device 16, shown in FIG. 9, respectively. In addition to it, they also have a database function for inspection parameters.

Figure 15:
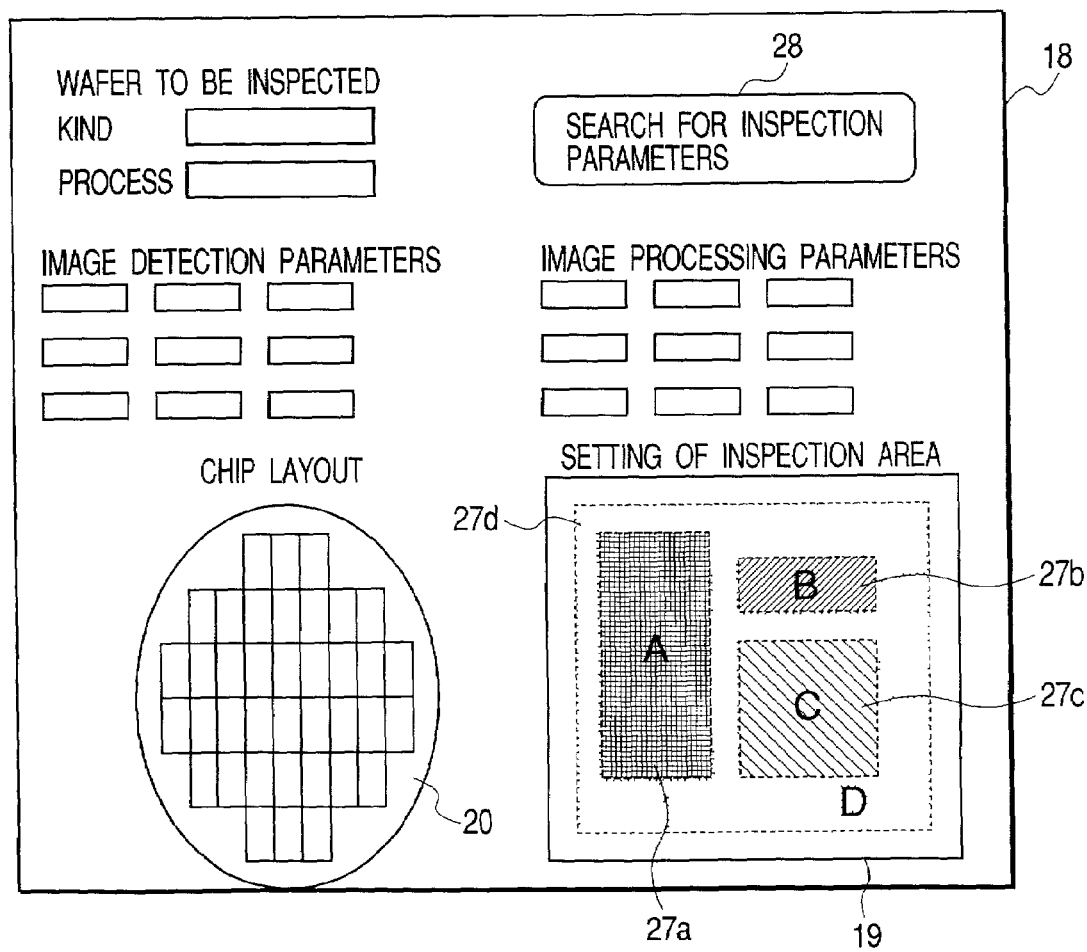
FIG. 15 is a diagram illustrating an inspection-parameter screen in the embodiment shown in FIG. 14.

FIG. 15 is a diagram illustrating an inspection-parameter setting screen 18 in this embodiment.

In the figure, the area 19 to be inspected is divided into function blocks 27*a*, 27*b*, 27*c* and 27*d*. The user searches whether or not inspection parameters of these function blocks 27*a* through 27*d* are registered in the image processing computer 17*a* and the storage device 16*a*, which have a database function for storing inspection parameters, by operating an inspection-parameter search button 28 on the screen 18 using a cursor (not shown in the figure). If the inspection parameters have already been registered, the user diverts them. Only if the inspection parameters are not registered, the use sets and registers inspection parameters newly.

It is to be noted that although the area 19 to be inspected is divided in response to density of a pattern in the embodiment shown in FIG. 9, there may also be a case where it is desirable to divide the area to be inspected in response to criticality of the area. For example, in a contact-hall formation process, etc., there may be a case where it is desirable to change inspection conditions not in response to density of hole placement, but in response to a position, that is to say, a hole position or the other positions. In such a case, a degree of criticality of the area to be inspected 19 is determined according to layout data, and the inspection conditions may be changed in response to the criticality. More specifically, an area, on which a hole has been placed according to layout data, is determined. The area is treated as a partial inspection area.

Figure 16:
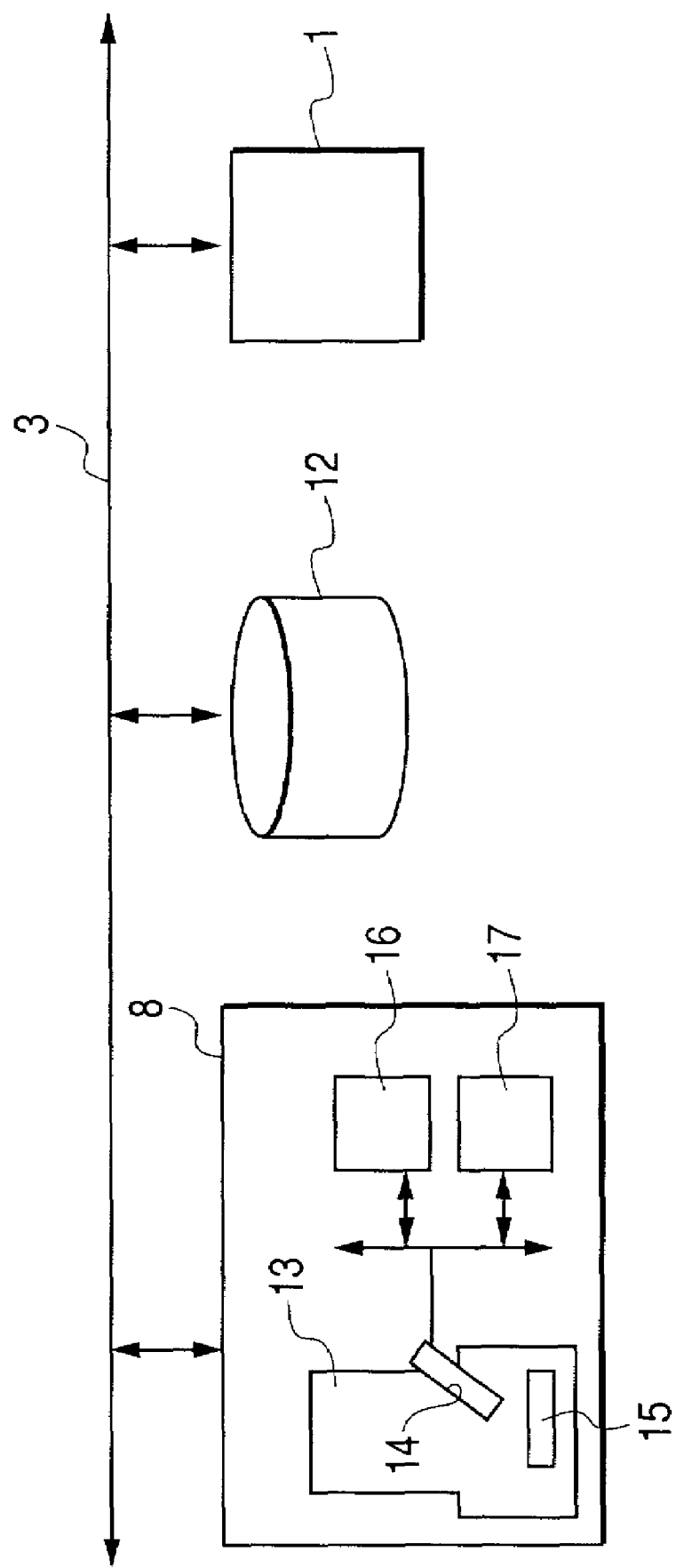
FIG. 16 is a block diagram illustrating a defect inspecting apparatus and a defect inspecting system used for inspecting an electronic circuit pattern according to a third embodiment of the present invention.

FIG. 16 is a configuration diagram illustrating a defect inspecting apparatus and a system, which are used for inspecting an electronic circuit pattern, according to a third embodiment of the present invention. Similar reference numerals have been used for similar parts corresponding to the figure.

In the figure, in the third embodiment, the electron-beam defect reviewing apparatus 8 is also connected to the network 3. As is the case with the pattern inspecting apparatus 1 in FIG. 9, this defect reviewing apparatus 8 also comprises the scanning electron microscope 13, the image detector 14, the storage device 16, and the image processing computer 17. The defect reviewing apparatus 8 targets the semiconductor wafer 15, of which a defect position is already known as a result of an inspection by the pattern inspecting apparatus 1, and detects an image at the defect position again for the purpose of observing the defect in more detail. To be more specific, the pattern inspecting apparatus 1 is the same as the pattern inspecting apparatus 1 shown in FIGS. 9 and 14. Therefore, the defect position on the semiconductor wafer 15, which has been detected by the pattern inspecting apparatus 1, is transferred to the defect reviewing apparatus 8 as inspection result information. In this case, the inspection-result information is text information, and includes X, Y coordinate information of a defect, and a defect ID.

When acquiring an image at each defect position recorded in the inspection-result information, and when acquiring an image of each defect, the defect reviewing apparatus 8 determines inspection parameters such as image-pickup magnification in response to characteristics (cell/non-cell, pattern density, etc.) of an area where there is the defect. For this reason, before image detection, layout data is transferred from the design information server 12. The user inputs a kind and a process of a product to be inspected on an operation screen of the defect reviewing apparatus 8. The defect reviewing apparatus 8 searches the design information server 12 for layout data of the targeted kind and process.

The defect reviewing apparatus 8 divides the area to be inspected into a cell portion and a non-cell portion according to the transferred layout data.

In this embodiment, an inspection parameter (image detection mode) is changed in the cell portion and the non-cell portion. Meaning of the inspection parameter and a purpose of the change for each position will be described.

The image detection mode is a parameter for specifying whether or not a reference image is detected. The cell portion includes the same repeated patterns. Therefore, if an image of the cell portion is picked up and stored beforehand, it is not necessary to detect the reference image for each defect ID every time, and it is possible to use the stored image as the reference image repeatedly. When trying to detect a reference image newly, it is necessary to perform the following steps: moving a stage, on which a semiconductor wafer to be inspected is placed, to a desired position; and irradiating an image-pickup area with an electron beam to detect an image. Therefore, as compared with a case where the reference image stored in the storage device 16 is diverted repeatedly, longer time will be required. Therefore, as regards a mode in which a reference image is diverted, it is advantageous because inspection time can be shortened to a large extent. Hereinafter, a mode, in which a reference image is stored and diverted, is called "reference-image reserve mode"; and a mode, in which a reference image is detected for each defect id every time, is called "reference-image detection mode". Setting the "reference-image reserve mode" and the "reference-image detection mode" for a cell area and a non-cell area respectively in an area to be inspected permits a inspection time to be shortened to a large extent.

As described above, the inspection time can be shortened by automatically dividing an area to be inspected into a cell portion and a non-cell portion according to the layout data, and by switching an inspection mode in each area.

Next, a defect inspecting apparatus and a system, which are used for inspecting an electronic circuit pattern, according to a fourth embodiment of the present invention will be described with reference to FIGS. 17 through 19.

A feature of the fourth embodiment is to restrain occurrence of a false report, which occurs frequently in the case of a specific pattern.

Figure 17:
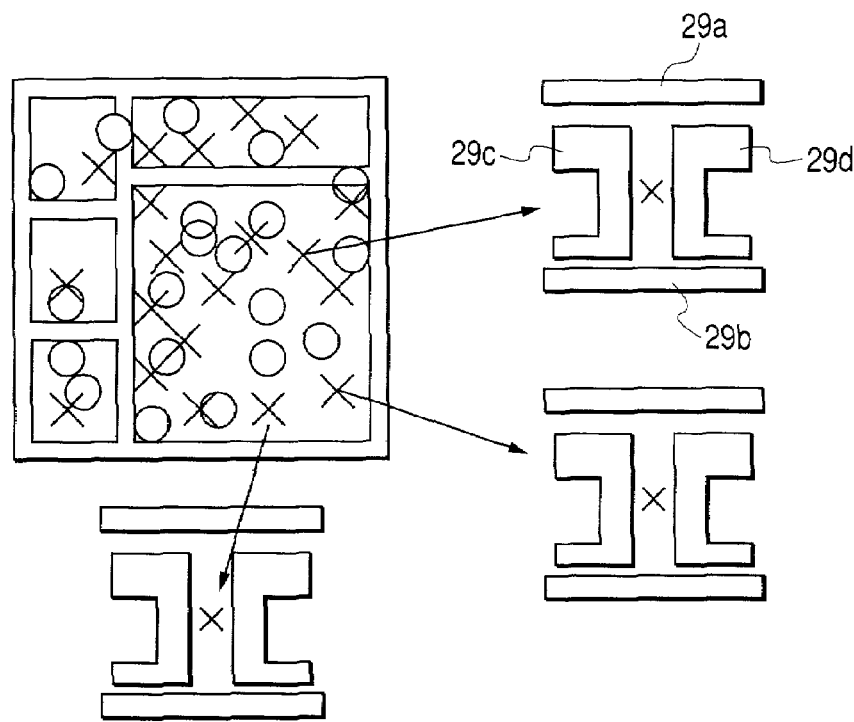
FIG. 17 is a diagram illustrating a state in which false reports caused by a specific pattern are scattered.

As shown by a symbol "X" in FIG. 17, if the problematic specific patterns, which cause a false report to occur frequently, exist in a scattered manner in a chip, it is not possible to judge whether or not a false report is caused by the same specific pattern, using a defect distribution map at a chip scale. For this reason, occurrence of a false report can be restrained by utilizing layout data to identify a pattern, which causes a false report to occur frequently, and by changing inspection sensitivity in a problematic pattern portion.

Figure 18:
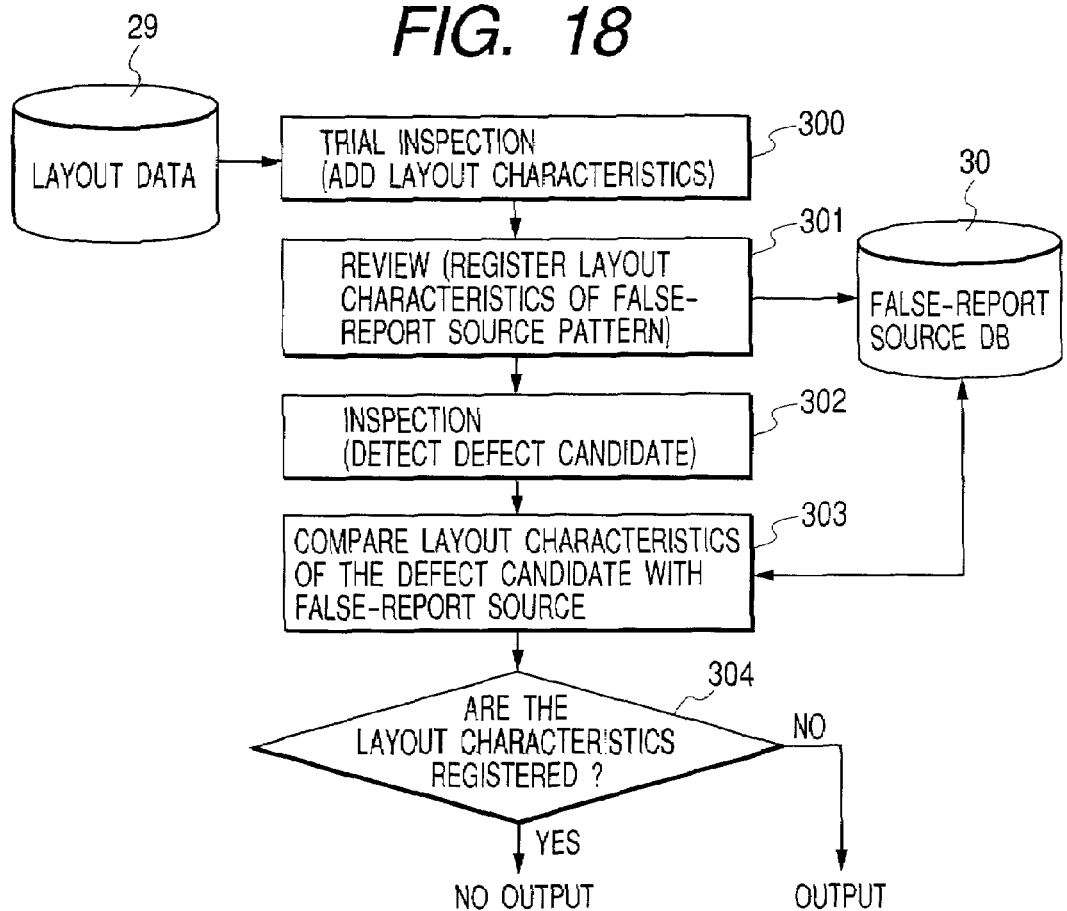
FIG. 18 is a flowchart illustrating a process flow of a defect inspecting apparatus and a defect inspecting system used for inspecting an electronic circuit pattern according to a fourth embodiment of the present invention.

FIG. 18 is a flowchart illustrating a process flow for this purpose.

Figure 25:
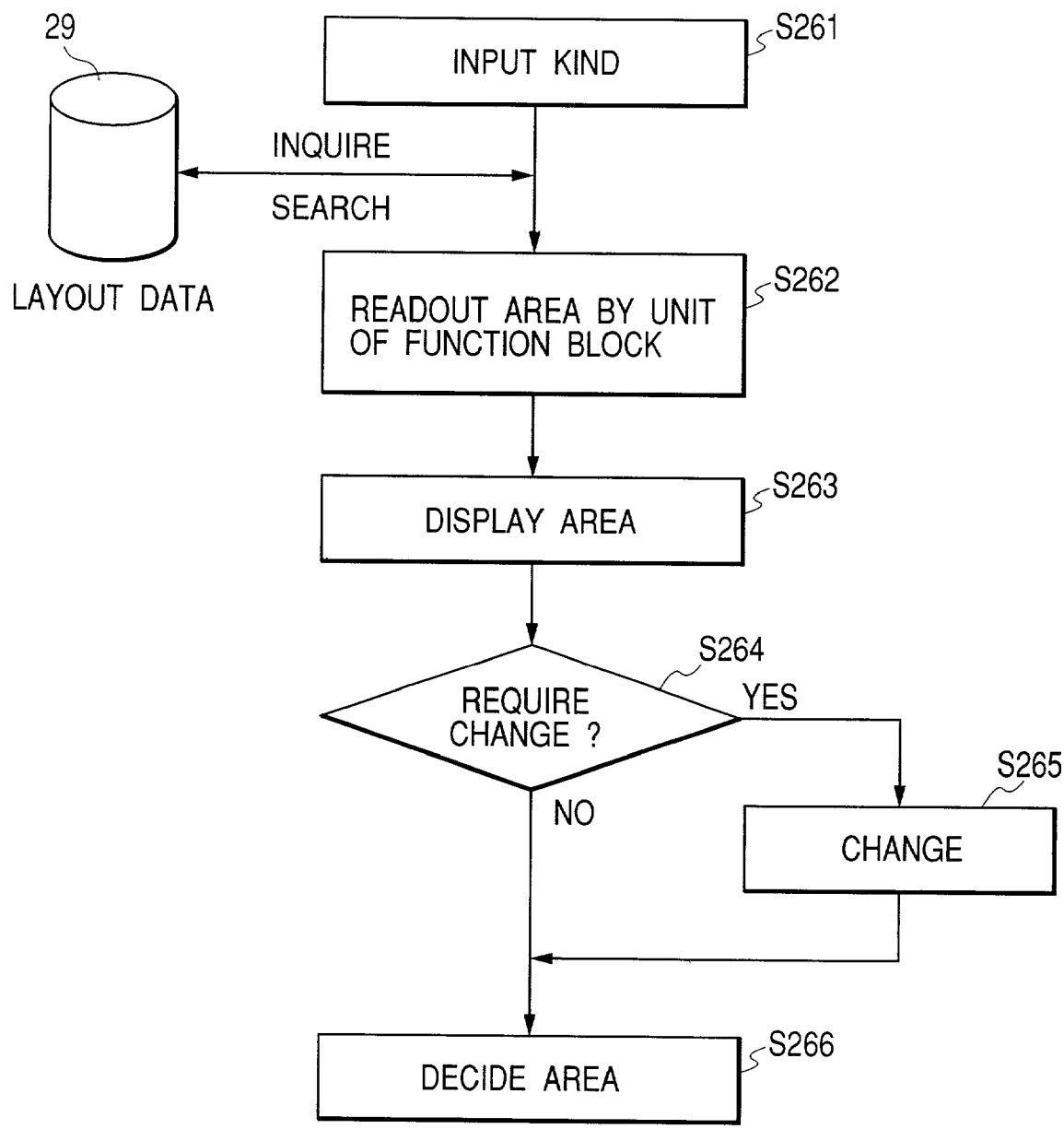
FIG. 25 is a flowchart illustrating a process flow for setting partial inspection areas.

In the figure, in the first place, at the time of executing trial inspection that is equivalent to the step 204 in FIG. 25 (step 300), if a defect is detected, a layout data 29 is referred to, and then information about a pattern, which has caused this defect, is obtained. More specifically, the information includes coordinates of a defect, a position and a shape of a pattern in proximity to the defect, and positional relation of the defect. In an example shown in FIG. 17, positions and shapes of patterns 29a, 29b, 29c and 29d in proximity to defects shown by the symbol "X", and positional relation with the defects (that is to say, between patterns 29a and 29b, and between patterns 29c and 29d), are coded and output as supplementary information about the defects. Hereinafter, it is referred to as layout characteristics of a defect.

After executing trial inspection, the user instructs as to whether or not it is a false report caused by a specific pattern, for each detected defect. For a false report, which is judged by the user to be a false report caused by the specific-pattern, layout characteristics for this false report are registered as layout characteristics of the specific pattern that causes the false report. Hereinafter, it is referred to as false-report source pattern database 30. FIG. 17 shows that a false report occurred in a pattern portion having the same layout.

Figure 19:
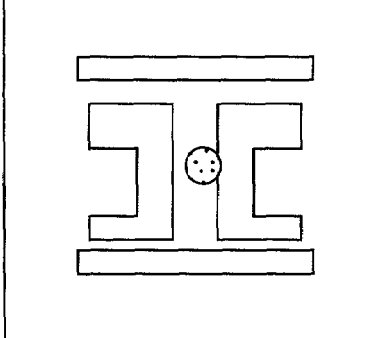
FIG. 19 is a diagram illustrating one exemplification of an interface screen for instructing a false report source pattern in a process shown in FIG. 18.

FIG. 19 shows one exemplification of such a user interface screen for instruction. When the user selects a false report caused by a specific pattern from a list of defects, which have been detected with the user interface screen for instruction, layout characteristics of the false report caused by the specific pattern are registered in the false-report source database 30 (step 301).

Next, when executing inspection (step 302), layout data is referred to, and then layout characteristics of a detected defect candidate are calculated. After that, whether or not the calculated layout characteristics are registered in the false-report source pattern database 30 as a false report source is checked by a search (step 303). If the calculated layout characteristics have already been registered (step 304), it is judged to be a false report, and it is not output as a defect. In FIG. 18, a defect caused by a specific pattern, which will become a false report source, is not detected. However, for example, even at a position, which will cause a false report source, output conditions as a defect may be changed in a specific pattern portion as follows: a defect having a size greater than or equal to a fixed value is output as a defect; a defect having brightness greater than or equal to a fixed value is output as a defect, or the like.

As described above, it is possible to utilize layout data to identify a pattern, which causes a false report to occur frequently, and thereby to restrain a false report in a problematic pattern portion.

Figure 20:
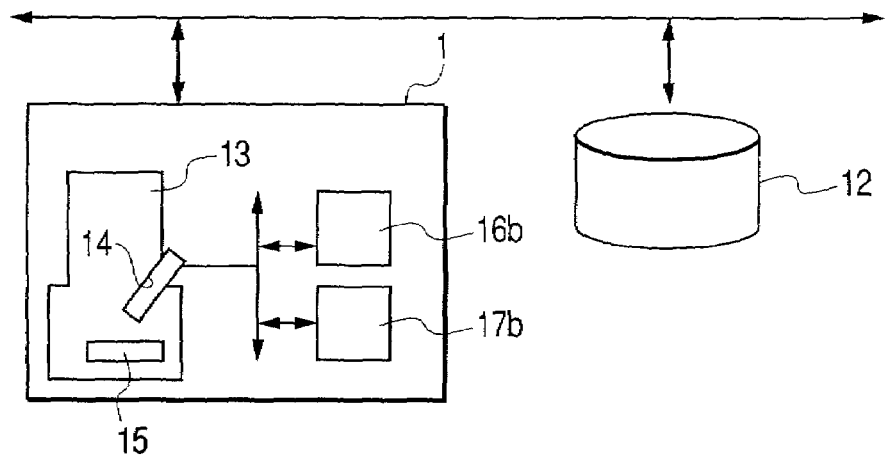
FIG. 20 is a block diagram illustrating of a defect inspecting apparatus and a defect inspecting system used for inspecting an electronic circuit pattern according to a fifth embodiment of the present invention.

FIG. 20 is a configuration diagram illustrating a defect inspecting apparatus and a system, which are used for inspecting an electronic circuit pattern, according to a fifth embodiment of the present invention. Reference numeral 16a denotes a storage device; and 17b denotes an image-processing computer. Similar reference numerals have been used for similar parts corresponding to FIG. 9.

As is the case with the first embodiment shown in FIG. 9, in the fifth embodiment, an area to be inspected (for example, the area 19 to be inspected in FIG. 10) is divided into partial inspection areas, each of which has a different inspection parameter. In addition to it, an inspection parameter is automatically optimized for each of the partial inspection areas. If the number of partial inspection areas becomes large, it is important in particular.

In FIG. 20, the image processing computer 17b and the storage device 16b have the same functions as the image processing computer 17 and the storage device 16 in FIG. 9. However, in addition to it, the storage device 16b also has a function of storing a detected image; and the image processing computer 17b also has a function of processing an image stored in the storage device 16b. In other words, an image is stored while image detection operation is performed; and offline image processing for this stored image is also performed.

When executing inspection, the image detector 14 detects an image of the semiconductor wafer 15 as an object to be inspected. The image processing computer 17b performs image processing for the detected image using also the storage device 16b, and then detects the defect to output it. On the other hand, when adjusting an inspection parameter, the image, which has been detected by the image detector 14, is temporarily stored in the storage device 16. As described below, the image-processing computer 17 automatically optimizes an inspection parameter for each partial area.

The automatic optimization of an inspection parameter automates a process of manual operation under the present conditions. As regards the parameter optimization by manual operation, in the first place, the user sets adjustment conditions for an inspection parameter temporarily. Originally, it is desirable to detect all defects, which require detection, without detecting a false report. However, in reality, if sensitivity is set high, not only true defects but also many false reports will be included. Therefore, the following operation is repeated: at the time of first trial inspection, increasing sensitivity to some degree so as to be more than necessary, and executing trial inspection; and executing trial inspection again while decreasing sensitivity so that a total number of detected defects including a false report becomes a fixed value or less as a result of the decrease of sensitivity. The steps described above can be arranged as follows.

(1) Set initial values of inspection conditions.

(2) Perform image processing for a detected image group, which has been stored, under inspection conditions that have been set temporarily.

(3) Compare an inspection result with convergence conditions of a parameter. In this case, for example, the following examples are named as the convergence conditions of the parameter:

(i) Detection sensitivity is highest within a range that a total number of the detected defects is a fixed value or less.

(ii) Detection sensitivity is highest within a range that density of detected defects is a fixed value or less.

(iii) Detection sensitivity is highest within a range that a false-report rate is a fixed value or less.

(iv) Concerning a plurality of specified defect points, detection sensitivity is lowest within a range that detection rate is a fixed value or more.

(4) If the convergence condition is satisfied, finish parameter adjustment.

(5) If the convergence condition is not satisfied, change the parameter by predetermined quantity, and perform the processing from (2) again.

The steps described above can be automated by the user's settings of the following (1) through (3) beforehand:

(1) Initial value of inspection parameter (2) Convergence condition of inspection parameter adjustment (3) Changed quantity of inspection parameter, which is applied when the convergence condition is not satisfied.

Figure 21:
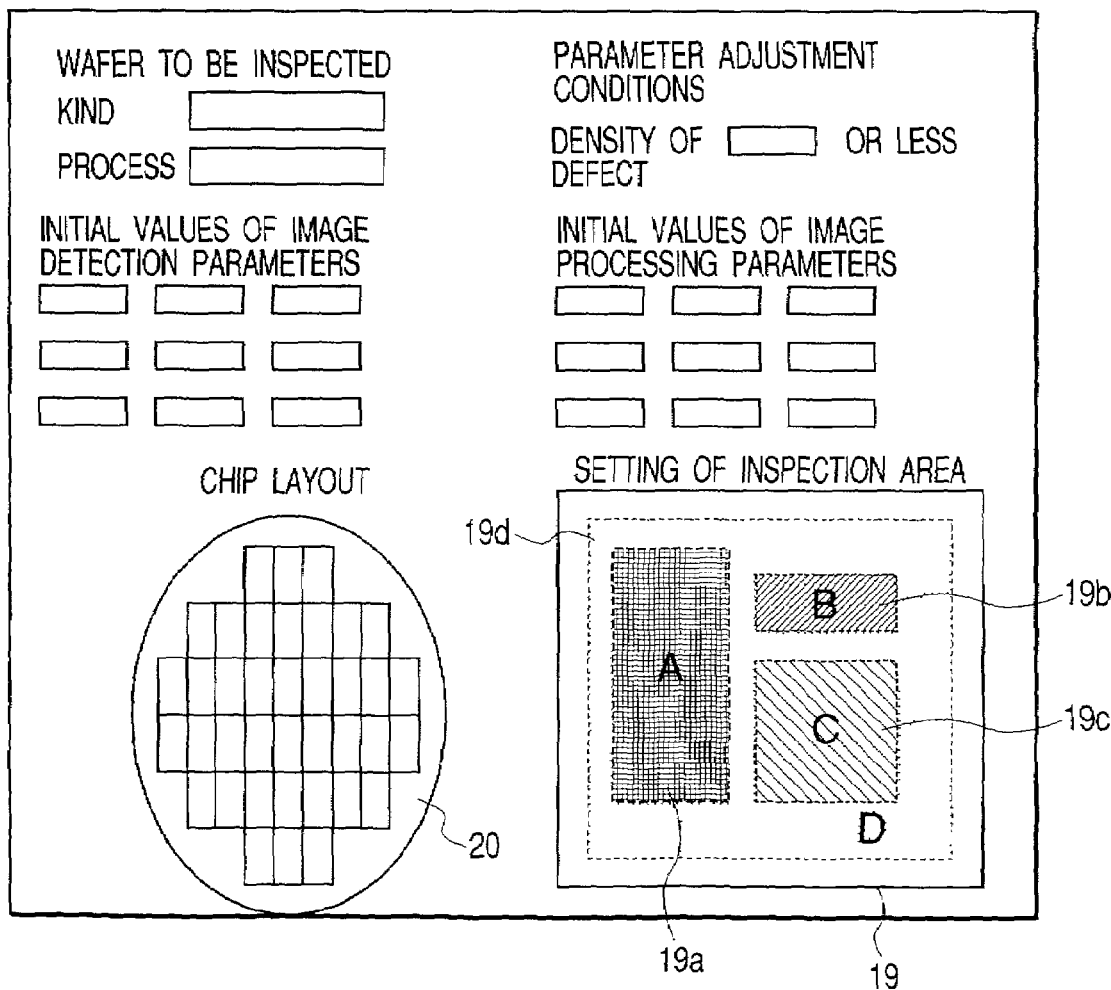
FIG. 21 is a diagram illustrating an inspection-parameter screen in the embodiment shown in FIG. 20.

FIG. 21 shows a setting screen of inspection conditions in the fifth embodiment. Setting an initial value of an inspection parameter and a convergence condition of the inspection parameter for each partial inspection area by the user permits the inspection parameter to be optimized automatically.

As described above, according to the present invention, an area to be inspected is divided into partial inspection areas in response to difference in inspection conditions. Therefore, man-hours for setting partial inspection areas can be reduced to a large extent, which enables the user to inspect the area to be inspected in such a manner that each of the partial inspection areas is inspected under the most suitable inspection condition.

Moreover, explosive increase in the number of detected defects, which are caused by inspection with detection sensitivity adapted to a portion having the densest pattern, can be avoided.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A system for inspecting a defect of an electronic circuit pattern formed on a semiconductor wafer, comprising:
    an inspection area setting unit which divides an area to be inspected into at least two partial inspection areas on the semiconductor wafer, each of which has each of different inspection conditions;
    an inspection condition setting unit which sets each inspection condition for each partial inspection area that is set by the inspection area setting unit;
    an image acquiring system which acquires an image signal from the each partial inspection area on the semiconductor wafer; and
    an inspection executing unit which executes an inspection to detect the defect by image-processing the image signal acquired by the image detection acquiring system under the each inspection condition which have been set by the inspection condition setting unit, for each partial inspection area set by the inspection area setting unit,
    wherein the inspection area setting unit divides the area to be inspected into at least the two partial inspection areas including a cell area and a non-cell area according to layout data, and the inspection condition setting unit sets conditions for the image acquiring system not to detect a reference image for each partial image in the cell area and to detect a reference image for each partial image in the non-cell area.

2. A defect-inspection control system for inspecting a defect of an electronic circuit pattern according to claim 1, wherein the inspection area setting unit comprises a display screen for overlaying at least one of a defect distribution map showing distribution of defect positions, a layout pattern, and a detected image of the area to be inspected, on an inspection area setting state, or for displaying at least one of them and the inspection area setting state simultaneously.

3. A system for inspecting a defect of an electronic circuit pattern according to claim 1, wherein the inspection area setting unit divides the area to be inspected into a defect output area and a non-output area; and the inspection executing unit outputs a defect, which exists in the defect output area set by the inspection area setting unit.

4. A system for inspecting a defect of an electronic circuit pattern according to claim 1, wherein the inspection area setting unit calculates a range of each function block included in an area to be inspected according to the layout data, in order to set the partial inspection areas.

5. A system for inspecting a defect of an electronic circuit pattern according to claim 1, wherein the inspection area setting unit displays a layout pattern of a whole chip on an inspection area setting screen, and registers an area, which has been specified or has been edited by a user on the layout pattern, as the partial inspection area.

6. A system for inspecting a defect of an electronic circuit pattern according to claim 1, wherein the inspection area setting unit superimposes each of the partial inspection areas on the layout pattern to display them.

7. A system for inspecting a defect of an electronic circuit pattern according to claim 1, wherein the inspection area setting unit superimposes and displays at least two of: each of the partial inspection areas; the layout pattern; and a position where a defect occurred.

8. A system for inspecting a defect of an electronic circuit pattern according to claim 1, wherein the inspection executing unit classifies detected defects by kind of defect; and
the inspection area setting unit superimposes a position on the layout pattern, where the defect occurred, on the layout pattern by using symbols, which are unique to kinds of defects, to display them.

9. A system for inspecting a defect of an electronic circuit pattern according to claim 1, wherein the inspection executing unit classifies detected defects according to at least whether the defect is a true defect or a false report.

10. A system for inspecting a defect of an electronic circuit pattern according to claim 1, wherein the inspection condition setting unit automatically adjusts the each inspection condition for each partial inspection area until the false-report rate is equal to or less than a predetermined fixed value, or the detection rate of a specified defect is greater than or equal to a predetermined fixed value.

11. A system for inspecting a defect of an electronic circuit pattern formed on a semiconductor wafer, comprising:
an inspection condition setting unit which calculates peculiar inspection condition for each position of an area to be inspected on the semiconductor wafer;
an inspection area setting unit which divides the area to be inspected into partial inspection areas on the semiconductor wafer, each of which has the substantially same inspection conditions that are calculated by the inspection condition calculating unit;
an image acquiring system which acquires an image signal from the each partial inspection area on the semiconductor water; and
an inspection executing unit which executes an inspection to detect the defect by image-processing the image signal acquired by the image detection acquiring system under the each inspection condition which have been set by the inspection condition setting unit, for each partial inspection area set by the inspection area setting unit,
wherein the inspection area setting unit divides the area to be inspected into the partial inspection areas including a cell area and a non-cell area according to layout data, and the inspection condition setting unit sets conditions for the image acquiring system not to detect a reference image for each partial image in the cell area and to detect a reference image for each partial image in the non-cell area.

12. A defect-inspection control system for inspecting a defect of an electronic circuit pattern according to claim 11, wherein the inspection area setting unit comprises a display screen for overlaying at least one of a defect distribution map showing distribution of defect positions, a layout pattern, and a detected image of the area to be inspected, on an inspection area setting state, or for displaying at least one of them and the inspection area setting state simultaneously.

13. A system for inspecting a defect of an electronic circuit pattern according to claim 11, wherein the inspection area setting unit divides the area to be inspected into a defect output area and a non-output area; and
the inspection executing unit outputs a defect, which exists in the defect output area set by the inspection area setting unit.

14. A defect-inspection control system for inspecting a defect of an electronic circuit pattern according to claim 11, wherein the inspection condition setting unit automatically adjusts the each inspection condition for each partial inspection area until the false-report rate is equal to or less than a predetermined fixed value, or the detection rate of e specified defect is greater than or equal to a predetermined fixed value.

15. A method for inspecting a defect of an electronic circuit pattern formed on a semiconductor wafer, comprising:
a process for reading layout data of an electronic circuit pattern on the semiconductor wafer;
a process for dividing an area to be inspected into a plurality of partial inspection areas on the semiconductor wafer according to the read layout data, each of which has each of different inspection conditions;
a process for setting each inspection condition for each of the divided inspection areas;
a process for acquiring an image signal from the each partial inspection area by an image acquiring system;
a process for executing an inspection to detect the defect by image-processing the image signal acquired by the image acquiring system under the each inspection condition that are set for the each partial inspection area; and
a process for displaying an executed result of the inspection on a screen;
wherein in the process for setting each inspection condition, the each inspection condition for the each partial inspection area including a cell area and a non-cell area is set so that in the process for acquiring an image signal, not to detect a reference image for each partial image in the cell area and to detect reference image for each partial image in the non-cell area.

16. A method for inspecting a defect of an electronic circuit pattern according to claim 15, wherein in the process for dividing an inspection area into a plurality of inspection areas, the inspection area is divided into the plurality of inspection areas, each of which has different density of the electronic circuit pattern.

17. A method for inspecting a defect of an electronic circuit pattern according to claim 15, wherein the layout pattern, which has been divided into the plurality of layout patterns, is displayed on a screen.

18. A method for inspecting a defect of an electronic circuit pattern according to claim 15, wherein the layout pattern, which has been divided into the plurality of layout patterns, is identified for each divided area, and is displayed on a screen.

19. A method for inspecting a defect of an electronic circuit pattern according to claim 15, wherein in the process for dividing an inspection area into a plurality of inspection areas, a range of each function block included in an area to be inspected is calculated according to the layout data, and thereby the inspection area is divided into the function blocks.

20. A method for inspecting a defect of an electronic circuit pattern according to claim 15, wherein in the process for dividing an inspection area into a plurality of inspection areas, distribution of wiring density in an area to be inspected is calculated according to the layout data, and thereby the area to be inspected is divided into areas, each of which has the same calculated wiring density.

21. A method for inspecting a defect of an electronic circuit pattern according to claim 15, wherein in the process for dividing an inspection area into a plurality of inspection areas, an inspection area is divided into areas, each of which has different criticality.

22. A method for inspecting a defect of an electronic circuit pattern according to claim 15, wherein in the process for dividing an inspection area into a plurality of inspection areas, a layout pattern of a whole chip is displayed on a screen, in addition to it, the layout pattern is divided into areas, each of which has been specified by a user, and then the areas are registered.

23. A method for inspecting a defect of an electronic circuit pattern according to claim 15, wherein in the process for dividing an inspection area into a plurality of inspection areas, the inspection area, which has been divided into the plurality of inspection areas, is superimposed on the layout pattern to display them.

24. A method for inspecting a defect of an electronic circuit pattern according to claim 15, wherein in the process for dividing an inspection area into a plurality of inspection areas, from among the inspection area, which has been divided into the plurality of inspection areas, the layout pattern, and a position where a defect occurred, at least two of them are superimposed to display them.

25. A method for inspecting a defect of an electronic circuit pattern according to claim 15, wherein in the process for executing the inspection, the detected defects are classified by kind of defect; and in the process for displaying the executed result of the inspection on the screen, defect positions occurred on a layout pattern are superimposed on the layout pattern to display them, using symbols, which are unique to kinds of defects.

26. A method for inspecting a defect of an electronic circuit pattern according to claim 15, wherein in the process for executing the inspection, the detected defects are classified according to at least whether the defect is a true defect or a false report.

27. A method for inspecting a defect of an electronic circuit pattern according to claim 15, wherein the process for setting each inspection condition automatically adjusts the each inspection condition for each partial inspection area until the false-report rate is equal to or less than a predetermined fixed value, or the detection rate of a specified defect is greater than or equal to a predetermined fixed value.

* * * * *